(12) United States Patent
Gupta

(10) Patent No.: US 12,380,585 B2
(45) Date of Patent: Aug. 5, 2025

(54) TISSUE IMAGING SYSTEM AND METHOD FOR TISSUE IMAGING

(71) Applicant: BEST MEDICAL INTERNATIONAL, INC., Springfield, VA (US)

(72) Inventor: Vineet Gupta, Wexford, PA (US)

(73) Assignee: Best Medical International, Inc., Springfield, VA (US)

( * ) Notice: Subject to any disclaimer, the term of this patent is extended or adjusted under 35 U.S.C. 154(b) by 561 days.

(21) Appl. No.: 15/960,249

(22) Filed: Apr. 23, 2018

(65) Prior Publication Data
US 2018/0308247 A1      Oct. 25, 2018

Related U.S. Application Data

(60) Provisional application No. 62/490,021, filed on Apr. 25, 2017.

(51) Int. Cl.
A61B 6/00      (2024.01)
A61B 6/02      (2006.01)
(Continued)

(52) U.S. Cl.
CPC .............. *G06T 7/62* (2017.01); *A61B 6/025* (2013.01); *A61B 6/12* (2013.01); *A61B 6/4233* (2013.01);
(Continued)

(58) Field of Classification Search
CPC .............. A61B 10/0233; A61B 10/04; A61B 2010/045; A61B 2034/107; A61B 34/10; A61B 6/025; A61B 6/12; A61B 6/4233; A61B 6/466; A61B 6/502; A61B 6/5205; A61B 6/5247; A61B 8/0825; A61B 8/0841; A61B 8/4254; A61B 8/4444;
(Continued)

(56) References Cited

U.S. PATENT DOCUMENTS 6,961,405 B2    11/2005   Scherch
7,289,227 B2    10/2007   Smetak et al.
(Continued)

OTHER PUBLICATIONS

International Search Report, Written Opinion of the International Searching Authority, and Search History, for PCT/US18/29182, Aug. 31, 2018, 16 pages.
(Continued)

*Primary Examiner* — Christopher L Cook

(57) ABSTRACT

The tissue imaging system, incorporates an integrated X-Ray and Ultrasound Imaging system. The X-Ray system is used for imaging and generating a 3D Volume of the extracted tissue sample (specimen). The Ultrasound imaging system is used for imaging the body area of interest of the patient from which the tissue sample is to be extracted. On the display of the system, the physician draws contours on the area of interest and the same is displayed as a 3D Volume. A 3D volume of the extracted tissue is generated using the x-ray imaging sub-system. Quantitative analysis is performed on the two 3D volumes (extracted tumor x-ray imaging and the contoured ultrasound imaging) to determine the difference between the contoured and the surgically extracted specimen to assist the physician in determining if further surgical intervention is required.

14 Claims, 25 Drawing Sheets

(51) Int. Cl.

| | |
|---|---|
| *A61B 6/12* | (2006.01) |
| *A61B 6/42* | (2024.01) |
| *A61B 6/46* | (2024.01) |
| *A61B 6/50* | (2024.01) |
| *A61B 8/00* | (2006.01) |
| *A61B 8/08* | (2006.01) |
| *A61B 10/02* | (2006.01) |
| *A61B 10/04* | (2006.01) |
| *A61B 34/10* | (2016.01) |
| *A61N 5/10* | (2006.01) |
| *G01N 23/046* | (2018.01) |
| *G01N 29/44* | (2006.01) |
| *G06T 7/00* | (2017.01) |
| *G06T 7/62* | (2017.01) |

(52) U.S. Cl.
CPC .............. *A61B 6/466* (2013.01); *A61B 6/502* (2013.01); *A61B 6/5205* (2013.01); *A61B 6/5247* (2013.01); *A61B 8/0825* (2013.01); *A61B 8/0841* (2013.01); *A61B 8/4254* (2013.01); *A61B 8/4444* (2013.01); *A61B 8/463* (2013.01); *A61B 8/466* (2013.01); *A61B 8/483* (2013.01); *A61B 8/5261* (2013.01); *A61B 10/0233* (2013.01); *A61B 10/04* (2013.01); *A61B 34/10* (2016.02); *A61N 5/1007* (2013.01); *A61N 5/1049* (2013.01); *G01N 23/046* (2013.01); *G01N 29/44* (2013.01); *G06T 7/0014* (2013.01); *A61B 2010/045* (2013.01); *A61B 2034/107* (2016.02); *A61N 2005/1024* (2013.01); *A61N 2005/1058* (2013.01); *G01N 2291/02475* (2013.01); *G06T 2207/10116* (2013.01); *G06T 2207/10136* (2013.01); *G06T 2207/20221* (2013.01); *G06T 2207/30096* (2013.01)

(58) Field of Classification Search
CPC ......... A61B 8/463; A61B 8/466; A61B 8/483; A61B 8/5261; A61N 2005/1024; A61N 2005/1058; A61N 5/1007; A61N 5/1049; G06T 2207/10116; G06T 2207/10136; G06T 2207/20221; G06T 2207/30096; G06T 7/0014; G06T 7/62
See application file for complete search history.

(56) References Cited

U.S. PATENT DOCUMENTS

| | | |
|---|---|---|
| 7,613,501 B2 | 11/2009 | Scherch |
| 9,138,193 B2 | 9/2015 | Lowe et al. |
| 2003/0149364 A1 | 8/2003 | Kapur et al. |
| 2006/0074287 A1 | 4/2006 | Neumann et al. |
| 2012/0150034 A1 | 6/2012 | DeFreitas et al. |
| 2015/0057546 A1 | 2/2015 | Yoon et al. |
| 2016/0045184 A1 | 2/2016 | Courtney et al. |
| 2016/0361036 A1 | 12/2016 | Ray et al. |
| 2017/0082557 A1* | 3/2017 | Iordache ................ G01N 23/04 |
| 2018/0078231 A1* | 3/2018 | Butani .................. G06T 7/0012 |
| 2018/0214086 A1* | 8/2018 | Park ........................ A61B 6/486 |
| 2018/0353145 A1* | 12/2018 | Simon ...................... A61B 6/54 |
| 2019/0236782 A1* | 8/2019 | Amit .................. A61B 10/0041 |
| 2019/0325617 A1* | 10/2019 | Kessener ............. G06T 11/005 |
| 2020/0352531 A1* | 11/2020 | Smith .................. H01J 35/065 |

OTHER PUBLICATIONS

Extended European Search Report, EP Application No. 18791194.6, corresponding to PCT/US2018029182, dated Mar. 5, 2021, 11 pages.
Examination Report issued in corresponding India Application No. 201917043056, dated Mar. 2, 2022, 6 pages.
Hearing Notice in corresponding India Application No. 201917043056, dated Feb. 16, 2024, 2 pages.
Intention to Grant in corresponding EP Application No. 18 791 194.6, dated May 8, 2023, 55 pages.
Invitation pursuant to Rule 63(1) EPC in corresponding Divisional EP Application No. 23 199 611.7, dated Dec. 14, 2023, 3 pages.
Supplementary European Search Report in corresponding EP Application No. 18791194.6, dated Dec. 2, 2020, 13 pages.
Office Action issued in corresponding Canadian Application No. 3,061,191, dated Sep. 25, 2024, 4 pages.

* cited by examiner

TISSUE IMAGING SYSTEM AND METHOD FOR TISSUE IMAGING

CROSS REFERENCE TO RELATED APPLICATION

This application claims priority under 35 U.S.C. § 119 to U.S. Provisional Patent Application No. 62/490,021, filed on Apr. 25, 2017, hereby incorporated herein by reference in its entirety.

FIELD OF THE INVENTION

The invention generally relates to the field of medical devices, and more particularly to tissue imaging devices, systems and methods utilizing both ultrasound imaging and X-ray imaging in the removal of cancerous, necrotic or other diseased tissue from a body, such as from a human body, animal body or reptilian body, and generating three dimensional (3D) ultrasound images and 3D X-ray images of tissue prior to and after its removal from the body to determine whether the desired amount or volume of the cancerous, necrotic or other diseased tissue has been removed from the body.

BACKGROUND

Imaging devices, such as using ultrasound imaging or X-ray imaging, are commonly used in diagnosis for treatment of various medical issues, such as injury to bones and detecting cancerous tissue in a body. One such use, for example, is the use of imaging type diagnostic tools in the detection of breast or prostate cancer, for example. Clearly, early detection of cancerous tissue and accurately removing such diseased tissue from a body can increase the likelihood of preventing the cancer from spreading or metastasizing throughout the body, as well as can minimize the need for additional surgical procedures involving excision of cancerous, necrotic or other diseased tissue.

The excising of cancerous, necrotic or other diseased tissue can, in some instances, be relatively complex, particularly to assure that the appropriate amount or volume of cancerous, necrotic or other diseased tissue, as typically also includes an amount of adjacent healthy tissue, is removed as an added precaution to minimize the re-occurrence or spreading in the body of the cancerous, necrotic or other diseased tissue. Pre-surgical diagnostics can employ X-ray imaging, for example, to determine the size, volume, and the location in the body of the cancerous, necrotic or other diseased tissue. The location of the tissue to be removed is appropriately marked, such as by a suitable marker or guidewire. Once the cancerous, necrotic or other diseased tissue is removed from the body, X-ray imaging, for example, typically can be employed to determine if the outer areas of the removed tissue do not include the cancer, or necrosis or other diseased tissue. Whereupon if it is determined from analysis of the diagnostic imaging of the removed tissue additional tissue needs to be removed, the above described procedure of tissue removal and diagnostic examination of the removed tissue is repeated, as necessary, until it is determined that the amount and volume of removed tissue is a correct amount.

X-ray imaging of removed tissue typically provides two dimensional (2D) images, with the removed tissue being rotated to obtain differing images thereof for the tissue analysis. However, traditional two dimensional (2D) X-ray imaging may be disadvantageous as typically involving a relatively long time period for analysis, as well as can likely increase the likelihood of inaccurate measurements, such as from movement of the tissue sample during X-ray imaging, and considering that it is typically performed under time constraints in relation to being performed during the time the person or animal is undergoing the surgical removal procedure. Another tissue analysis technique employed can involve digital tomosynthesis which utilizes digital image capture and processing with a detector motion providing images similar to conventional tomography, but typically the images can have a limited field depth, but can possibly save time for sample analysis in that image slices at various depths and thickness can be provided.

Considering the advantages and limitations of X-ray and digital tomosynthesis systems, a cabinet specimen tomosynthesis system has been proposed for specimen imaging in U.S. Pat. No. 9,138,193 to Lowe et al. issued on Sep. 22, 2015, entitled "Specimen Radiography With Tomosynthesis In A Cabinet" (the "'193 patent"), incorporated by reference herein in its entirety. In the '193 patent, X-ray imaging and digital tomosynthesis are utilized in a method and system for producing tomosynthesis images of a breast specimen in a cabinet x-ray system is disclosed.

In the '193 patent system, it is disclosed that an X-ray source delivers X-rays through a specimen of excised tissue and forms an image at a digital X-ray detector. Multiple X-ray images are taken as the X-ray source moves relative to the stationary breast specimen. It is disclosed that, desirably, the X-ray source moves in a range from about 350 degrees to and including about 10 degrees. The X-ray source can travel substantially along a path that generally defines an arc, or linearly, while the digital X-ray detector remains stationary throughout and the source remains substantially equidistant from the specimen platform. The '193 patent further discloses that the set of X-ray image data taken at the different points are combined to form a tomosynthesis image that can be viewed in different formats, alone or as an adjunct to conventional specimen radiography. The '193 patent further discloses reconstructing three-dimensional tomosynthetic x-ray images from two-dimensional projection x-ray images in real-time and on-demand.

While the cabinet specimen tomosythesis system disclosed in the '193 patent appears to offer advantages in specimen analysis, the disclosed '193 patent specimen analysis appears to rely primarily on human judgment in reading the images of the removed tissue to determine whether an appropriate amount of diseased tissue and adjacent non-diseased marginal tissue has been removed. Since the '193 patent system appears to rely on human judgment in the determination of the sufficiency of tissue removed, and which judgment appears to be based only on the reconstructed images of the excised tissue, the likelihood of error can potentially still be affected by one or more of the human reviewer and/or the quality or accuracy of the reconstructed image of the excised tissue. Further, it appears the '193 patent system image analysis does not provide a system and method for an image comparison of the excised tissue with that of the tissue to be removed as present in the body.

Further, ultrasound imaging has been employed in various medical applications to provide ultrasound images of various body portions and bodily tissue as, for example, in U.S. Pat. No. 6,961,405 to Scherch issued on Nov. 1, 2005 entitled "Method And Apparatus For Target Position Verification" (the "'405 patent"), incorporated by reference herein in its entirety.

In the '405 patent, a system and method is disclosed for aligning the position of a target within a body of a patient to a predetermined position used in the development of a radiation treatment plan. The apparatus includes an ultrasound probe used for generating live ultrasound images, a position sensing system for indicating the position of the ultrasound probe with respect to the radiation therapy device, and a computer system. The '405 patent apparatus discloses an ultrasound probe that generates two-dimensional ultrasound images of the portion of a patient's body containing the target, while patient is on a treatment table. The computer system is used to display the live ultrasound images of a target in association with representations of the radiation treatment plan, to align the displayed representations of the radiation treatment plan with the displayed live ultrasound images, to capture and store at least two two-dimensional ultrasound images of the target overlaid with the aligned representations of the treatment plan data, and to determine the difference between the location of the target in the ultrasound images and the location of the target in the representations of the radiation treatment plan.

Thus, the '405 patent system advantageously provides two-dimensional ultrasound images of the portion of a patient's body to align the displayed representations of the radiation treatment plan with the displayed live ultrasound images, so as to determine the difference between the location of the target in the ultrasound images and the location of the target in the representations of the radiation treatment plan. However, it appears the '405 patent system and method likewise does not specifically disclose a tissue imaging system and method for an image comparison of excised tissue from a body with that of the tissue to be removed as present in the body.

Also, various systems have been employed to track the position and orientation of an object in medical applications. In this regard, knowledge of the position of a surgical tool during neurosurgery or location of a target such as a tumor while radiation therapy treatment is occurring, have always been important considerations. The position of an object or tool is typically defined by three translation parameters (x, y, z) and three rotation parameters (pitch, roll, yaw) corresponding to six degrees of freedom. The translation parameters (x, y, z) indicate three-dimensional position, i.e. forward and back (y-axis), left and right (x-axis), up and down (z-axis), and three rotation parameters (pitch, roll, yaw) indicate orientation of the tool or object, e.g. rotation about the x-axis (pitch), rotation about the y-axis (roll), and rotation about to the z-axis (yaw).

Various systems are known for determining the spatial position and orientation of an object. One such system includes use of a mechanical arm to track the location of a medical tool or probe which can be used to further determine the location of a target. In order to locate the target, the tool or probe can be affixed to the mechanical arm having a known reference position. A computer system tracks the tool or probe while an operator repositions the tool or probe along with the mechanical arm. The geometry of the mechanical aim is known such that movement of the tool or probe in conjunction with the mechanical arm provides the computer system continuous position information regarding the tool or probe. In an invasive procedure, the tool or probe can have a fixed length. Thus, contacting the target with the end of the tool can provide a position location of the target. Ultrasound has also been employed to track the position and orientation of an object in medical applications. In a non-invasive procedure, a probe, such as an ultrasound device, can be used to locate both the position and the orientation of the target.

Also, both active and passive emission techniques are known which operate by projecting a geometric representation or extension of the object or tool formed by the emitters onto the field of view of a pair of spaced sensors. Various implementations of sensors have been used, one being the use of two cameras positioned spaced apart a known distance and angled in the general direction of the object or tool such that the three-dimensional position of the object or tool can be obtained by triangulation from the positions of the emitters. For example, a camera or opti-electrical motion measurement system, known as the Polaris®, by Northern Digital Inc., Ontario Canada, has been used for triangulating the position of optically trackable tools.

Specifically, a computer system, using mathematical processing, can determine the three dimensional coordinates of each one of the emitters associated with the object or tool. The position of each of the emitters can be used to determine the position of the object or tool relative to a three dimensional coordinate system centered at a preselected point in space, typically at a point fixed relative to the sensors. The positional relationship to each other of each of the emitters associated with the object or tool can be utilized to further determine the orientation in space of the object or tool. Generally, at least three of the emitters must be detected and must be unobscured by any adjacent emitters. Additionally, the sensors generally require the emitters to be a minimum distance, for example, 3-5 cm apart. In theory, such systems can provide three unobstructed emitters for most of a sphere created by the six degrees of freedom. One of the more modern types of passive emission system utilizes passive retro-reflectors which can be affixed to the object or tool and which reflect directly back to a pair of active emitter arrays adjacent a pair of optical sensors. This type of system allows the optical sensors to be positioned relatively close together.

For example, a system to track the position and orientation of an object, such as for medical applications in medical applications is described in in U.S. Pat. No. 7,289,227 to Smetak et al. issued on Oct. 30, 2007 entitled "System And Tracker For Tracking An Object, and Related Methods" (the "'227 patent"), incorporated by reference herein in its entirety.

In the '227 patent, there is disclosed a system to track a three-dimensional position and an orientation of a movable object and associated methods are provided. The system includes a tracker having an optically trackable body, adapted to connect to the movable object. A plurality of optical indicators are connected or mounted to the optically trackable body to forma a plurality of geometric figures. A plurality of obfuscating flanges optically separate the optical indicators from each other to prevent each of the optical indicators from becoming optically coincident with another optical indicator when viewed along a preselected viewing path. The system also includes an apparatus to track the tracker having an optical detector to simultaneously detect the three-dimensional position of at least three of the plurality of optical indicators and a determiner to determine the three-dimensional position and orientation of the optically trackable body from the position of the optical indicators.

However, it appears the '227 patent system and method, as well as the above referred to systems that have been employed to track the position and orientation of an object, such as in medical applications, likewise do not specifically disclose a tissue imaging system and method for an image comparison of excised tissue from a body with that of the tissue to be removed as present in the body.

It is believed that there is a need for a tissue imaging device, system and method that can enhance the accuracy and efficiency, as well as can assist in reducing the possibility of human error, in determining whether and appropriate amount of cancerous, necrotic or other diseased tissue has been removed from a body, such as of a person, animal or reptile. Also, in view of the foregoing, there is believed to be a need to provide a compact and versatile tissue imaging system as can readily provide assistance, such as to a human or veterinary surgeon or doctor, in real time, such as during a surgical procedure for the tissue removal to enhance the confidence level that a correct amount of the cancerous, necrotic or other diseased tissue has been removed from a body.

Further there is believed to be a need, as well as it would be advantageous to have, an integrated cabinet type, tissue imaging system for specimen imaging that provides generated 3D images of the removed and to be removed tissue and compare the generated 3D images of the removed and to be removed tissue to facilitate accurately indicating, such as to a surgeon in an operating room, that that the cancerous, necrotic or other diseased tissue, as well as an appropriate margin of heathy tissue around the cancerous, necrotic or other diseased tissue has been excised in an expedient manner and to enhance the probability of successful removal, while reducing the likelihood of human error.

Further, a tissue imaging device, system and method is believed to be needed that utilizes and combines the benefits of ultrasound imaging of bodily tissue and the benefits of X-ray imaging of specimens in the removal of cancerous, necrotic or other diseased tissue from a body, such as from a human body, animal body or reptilian body, so as to provide generated three dimensional (3D) ultrasound images of the tissue to be removed present in the body for comparison with generated 3D X-ray images of the removed tissue to increase the accuracy of the representations of the imaged tissue to facilitate the accuracy and ease of comparison in the determination of whether the desired amount or volume of the cancerous, necrotic or other diseased tissue has been removed from the body.

Thus, a compact, efficient, accurate and integrated tissue imaging device, system and method utilizing both ultrasound imaging and X-ray imaging in the removal of cancerous, necrotic outer diseased tissue from a body to facilitate determining whether an appropriate or correct amount or volume of cancerous, necrotic other diseased tissue has been removed from the body addressing, the aforementioned problems or shortcomings is desired.

SUMMARY OF INVENTION

An embodiment of a tissue imaging system includes an x-ray imaging subsystem and an ultrasound imaging subsystem. The x-ray imaging subsystem includes an x-ray tube, a digital flat panel, a specimen tray, x-ray beam generator & controller, x-ray angle controller, and x-ray analysis processor and memory to store x-ray images. The ultrasound imaging subsystem includes an ultrasound probe assembly (ultrasound probe attached to a holder with 3D infrared markers), a 3D infrared imaging camera, probe 3D position and orientation detector, ultrasound beamformer, and the ultrasound analysis processor and memory to store ultrasound images. The system also includes a computer having an image fusion processor and memory to perform ultrasound and x-ray 3D volume fusion and store results of fusion analysis. The computer also has a user interface device (monitor) to display results and control the system.

The method includes having the patient lie on the operating room (treatment) table, providing an ultrasound probe to perform ultrasound imaging of the area of interest and displaying the live ultrasound image. More specifically, as the ultrasound probe is moved and rotated, tracking the 3D position and orientation of the ultrasound probe and displaying the information on the user interface.

The method also includes the drawing of contours on the ultrasound images to mark the tissue structure to be extracted. These contours are drawn on the ultrasound images acquired at different probe orientations and positions. Advantageously, the ultrasound analysis processor in the computer generates a 3D volume of the ultrasound and the contoured tissue structure and provides measurement information that includes the height, width, length, and volume of the contoured tissue.

The method also includes extracting the tissue structure/specimen and placing it onto the specimen tray of the x-ray subsystem and performing x-ray imaging. More specifically, performing the x-ray imaging includes rotating the x-ray tube and the flat-panel detector around the stationary specimen in the specimen tray and acquiring multiple x-ray images and generating a 3D volume of the specimen from x-ray images. The x-ray analysis processor in the computer system provides measurement information that includes the height, width, length, and volume of the extracted specimen.

The method also includes fusion of the 3D volumes of the tissue contoured on the ultrasound image and the extracted tissue imaged via the x-ray subsystem by the fusion processor in the computer system. More specifically, overlaying one volume over the other for visual representation of the difference and performing quantitative analysis by determining/calculating the difference in volume, length, width and height of the two volumes. The visualization of 3D volumes overlaid on top of each other and the determined differences has the advantage of providing quantitative feedback on the error in specimen extraction facilitates preventing subjectivity in deciding on the amount of tissue to be extracted.

The method also includes performing biopsies under ultrasound guidance. The method enables marking of biopsy needles visualized in a 2D live ultrasound image and visualizing in a 3D ultrasound volume to provide an accurate representation of the angle and the position of the biopsy needle with respect to the structure being biopsied. In addition, the method provides the capability of visualizing all the biopsies performed on the tissue by displaying the needle paths of all biopsies in 2D and 3D ultrasound visualized on the user interface.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

Figure 1A:
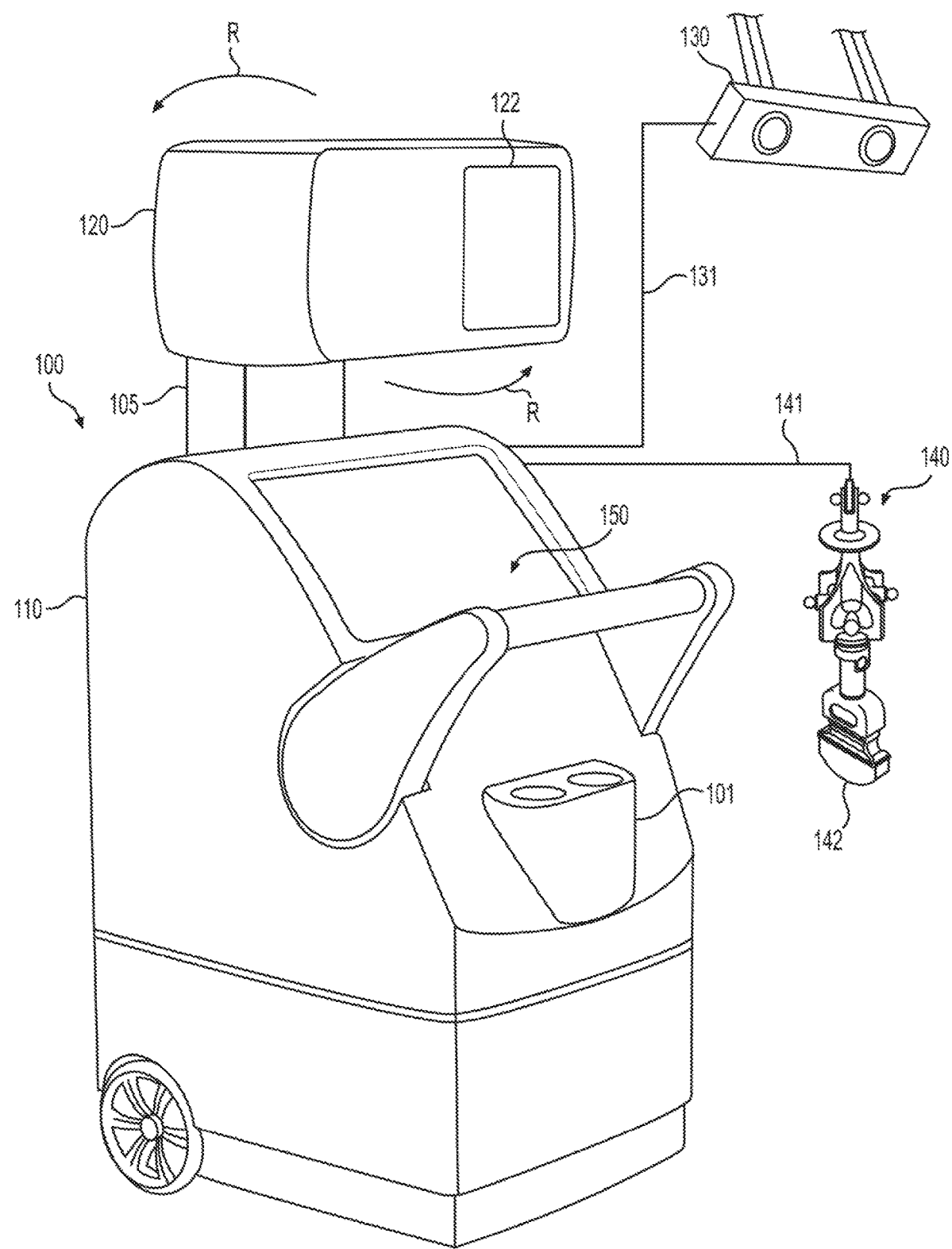
FIG. 1A is a perspective view of an embodiment of a tissue imaging system, according to the present invention.

Referring now to FIG. 1A, there is illustrated a tissue imaging system 100. The system 100 includes a main body 110, an X-Ray Chamber 120, a neck 105, an interface display 150, and an Infrared 3D Imaging Camera 130. The neck 105 connects the X-Ray Chamber 120 with the main body 110. The neck 105 also provides a support/anchor for the X-Ray Chamber 120 to rotate in the arrowed direction R about its central axis. The ultrasound probe with tracker system 140 includes or incorporates an ultrasound probe 142. Also, the imaging system 100 can include a holder 101 that can house an ultrasound probe and an ultrasound gel or other items for the imaging procedure, for example.

Figure 1B:
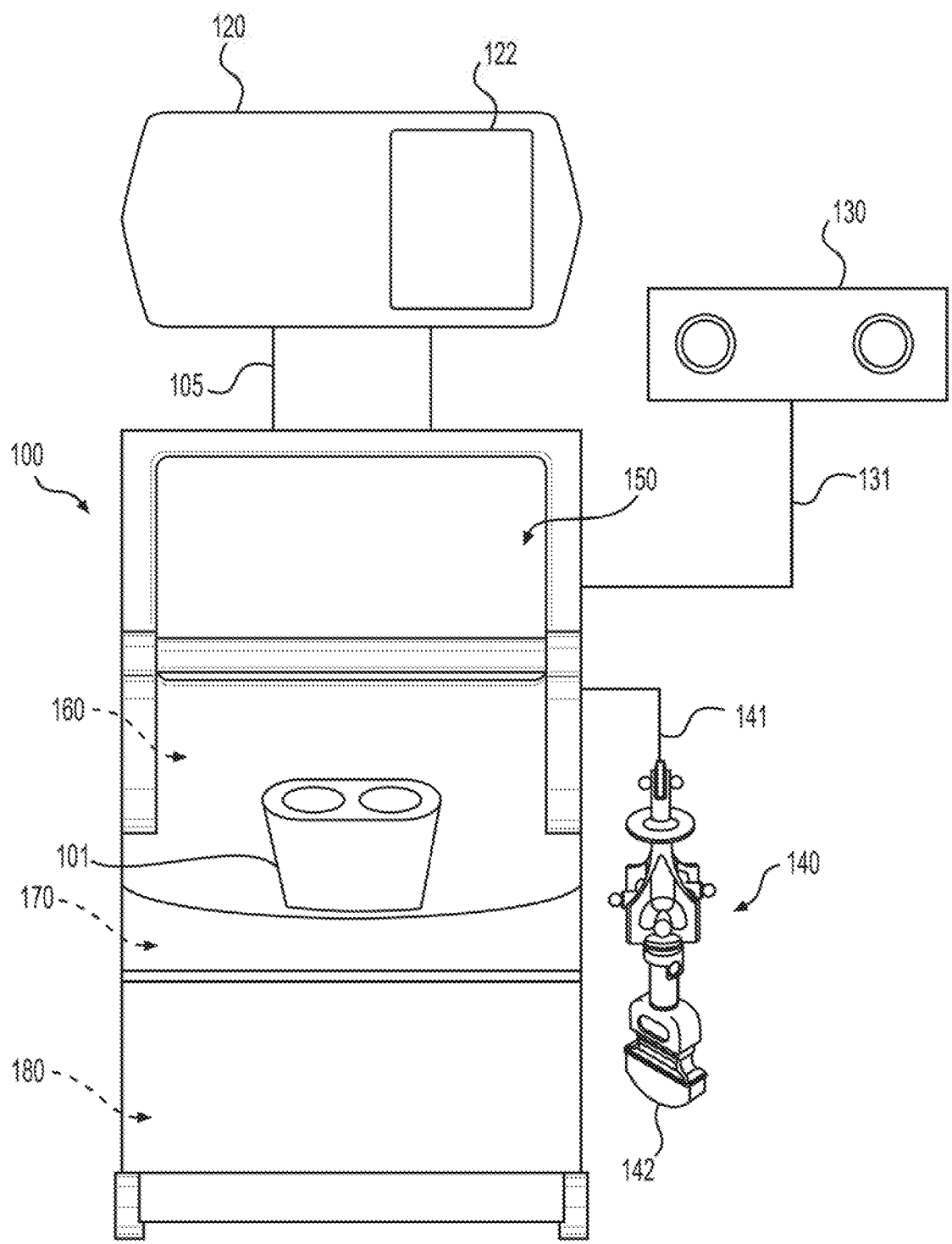
FIG. 1B is a schematic perspective view of an embodiment of the tissue imaging system of FIG. 1A, according to the present invention.

Referring to FIG. 1B, there is schematically illustrated the main body 110 that includes an X-Ray Generator, to be described, within the X-Ray Chamber 120, an X-ray controller system 160 for controlling various operations of the X-ray imaging generation and processing in the imaging system 100, an ultrasound beamformer system 170 for generating and processing ultrasound images and communicates via a wired or wireless communication 141 with the ultrasound probe with tracker system 140 and via a wired or wireless communication 131 with the infrared 3D Imaging Camera 130 in the imaging system 100. Also, the main body 110 includes an Image Comparison and Generation System 180 that communicates with the X-ray controller system 160 and with the ultrasound beamformer system 170 for control, imaging, visualization, measurement, comparison and analysis in the generation of the 2D and 3D ultrasound and X-ray images in the system 100, as schematically indicated in FIG. 1B.

Figure 2A:
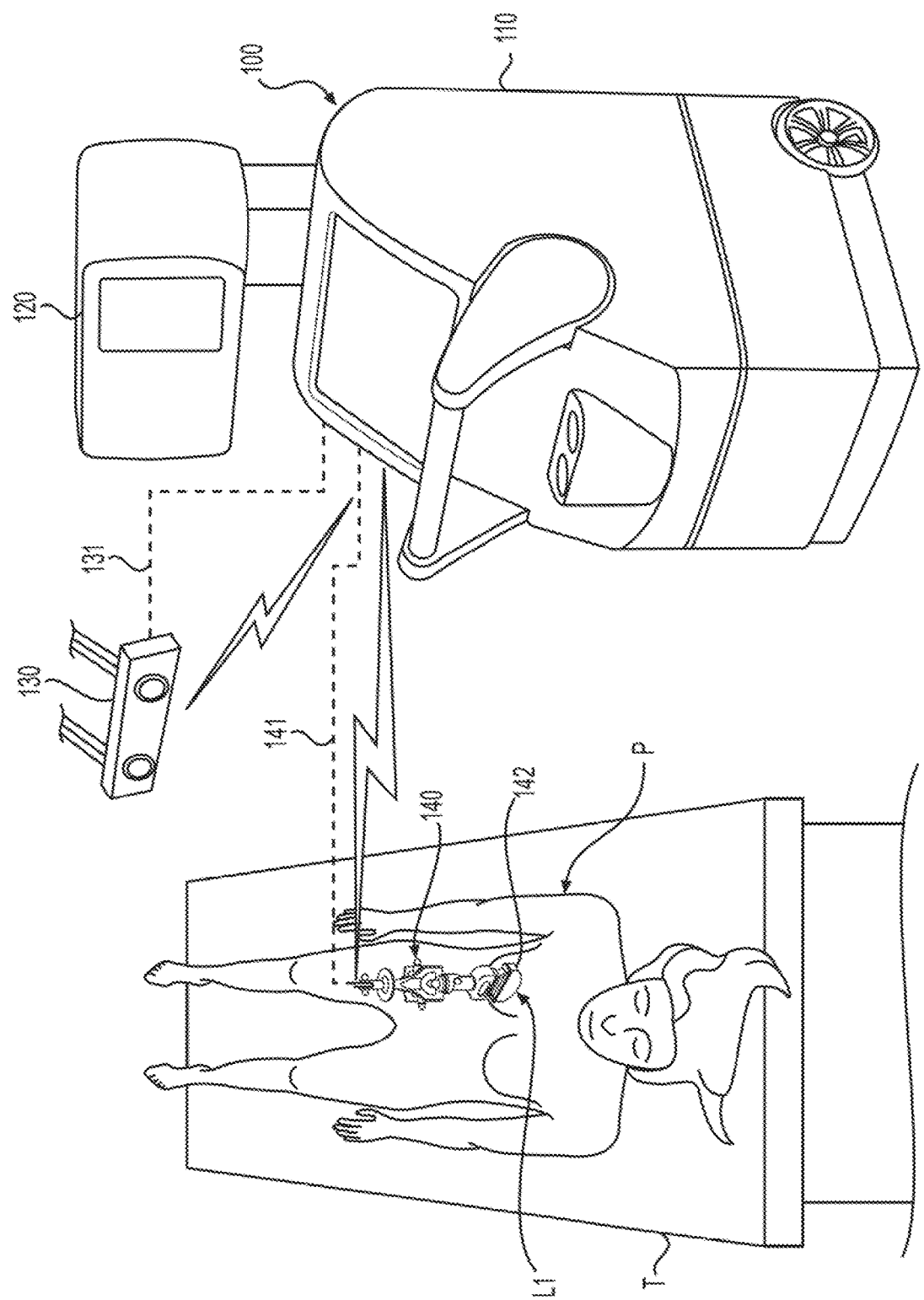
FIG. 2A is an environmental perspective view showing the tissue imaging system of FIGS. 1A and 1B obtaining ultrasound images of a portion of a body, according to the present invention.

Referring to FIG. 2A, the ultrasound probe with tracker system 140 can be connected via a wired or wireless connection to the main body 110. Similarly, the Infrared 3D Imaging Camera 130 can be connected to the main body 110 via a wired or wireless connection. FIG. 2A also shows the patient P lying supine on the Operating Table T with the ultrasound probe 142 imaging the breast at location L1.

Figure 2B:
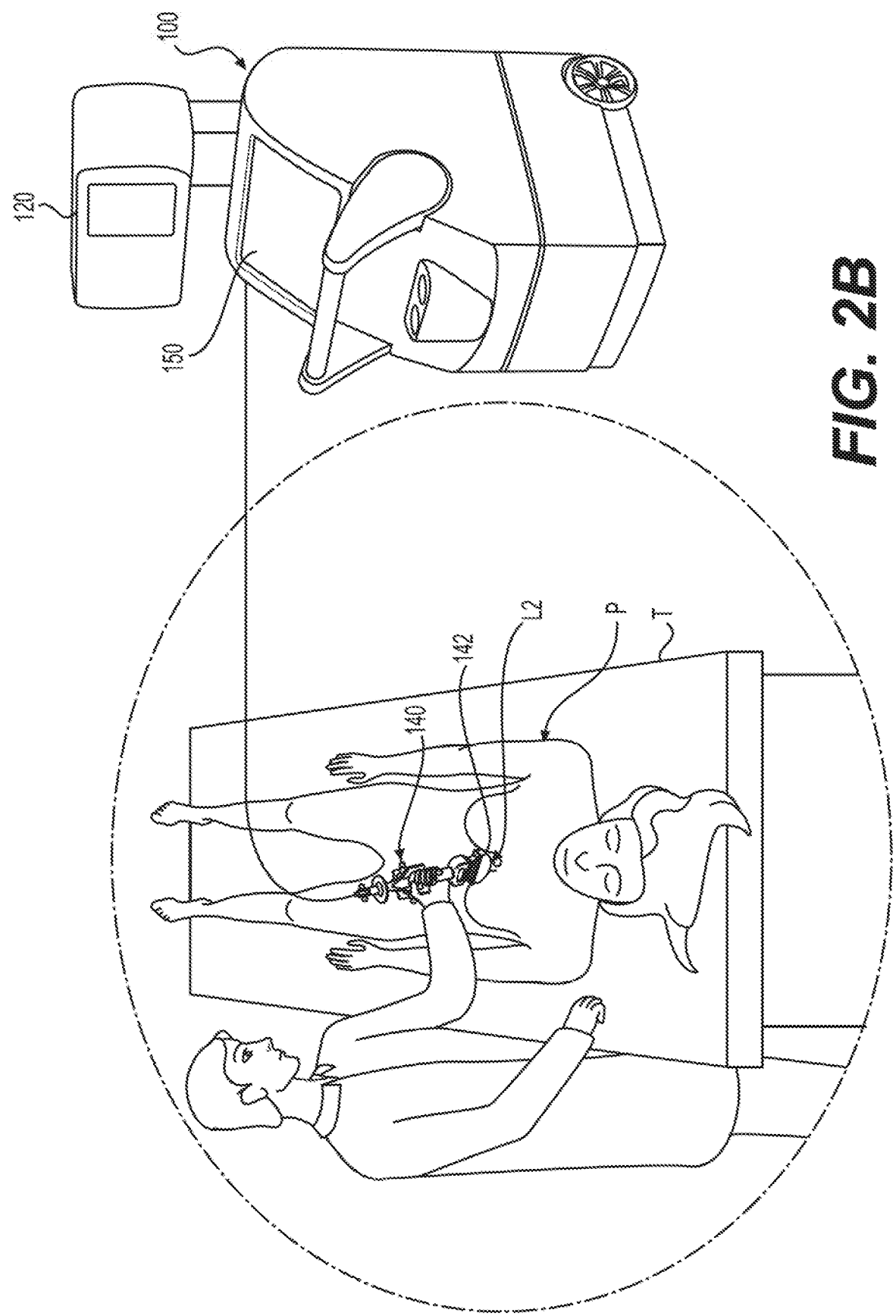
FIG. 2B is an environmental perspective view showing an embodiment of the tissue imaging system of FIGS. 1A and 1B obtaining ultrasound images of another portion of a body, according to the present invention.
Figure 2C:
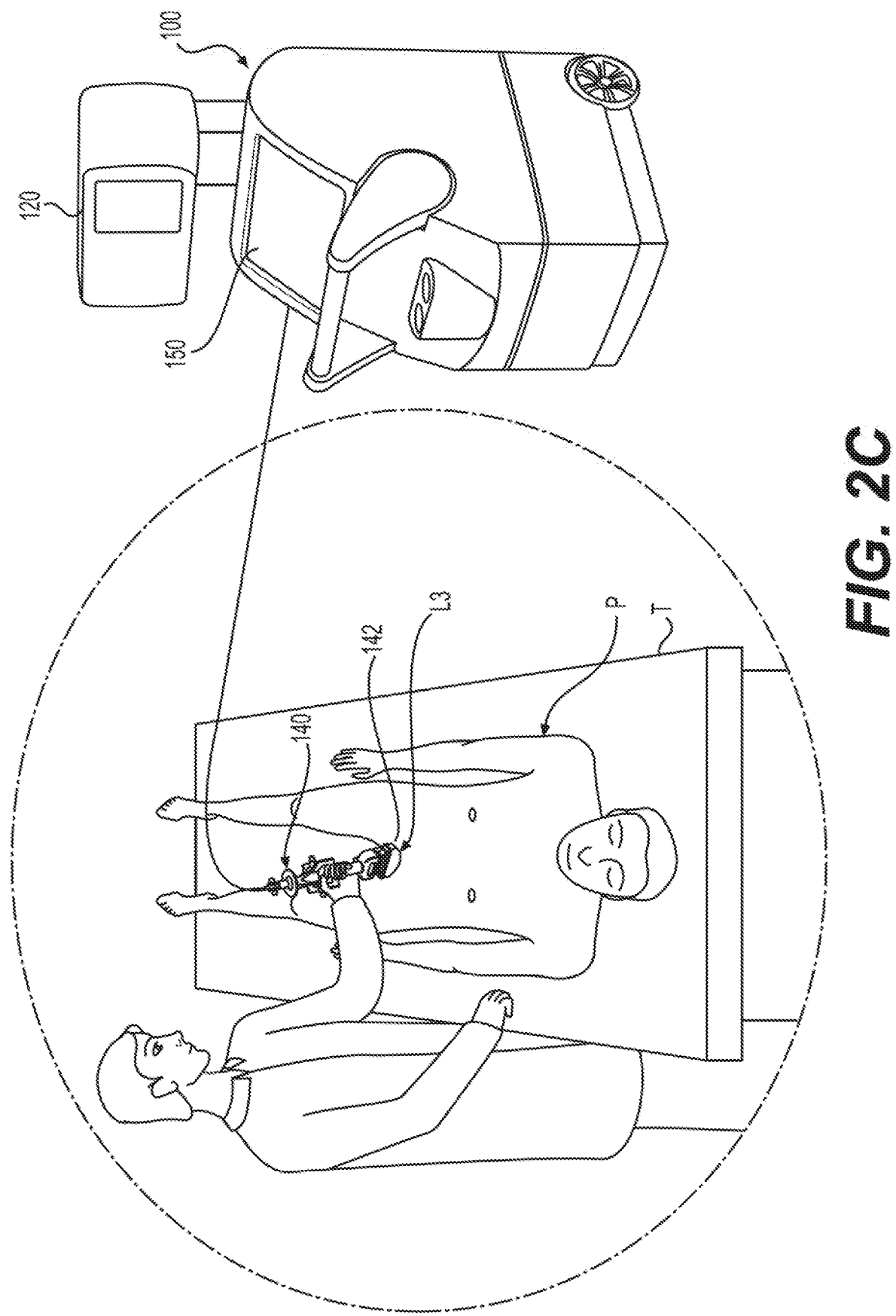
FIG. 2C is an environmental perspective view showing an embodiment of the tissue imaging system of FIGS. 1A and 1B obtaining ultrasound images of a portion of a body in the area of the prostrate, according to the present invention.
Figure 2D:
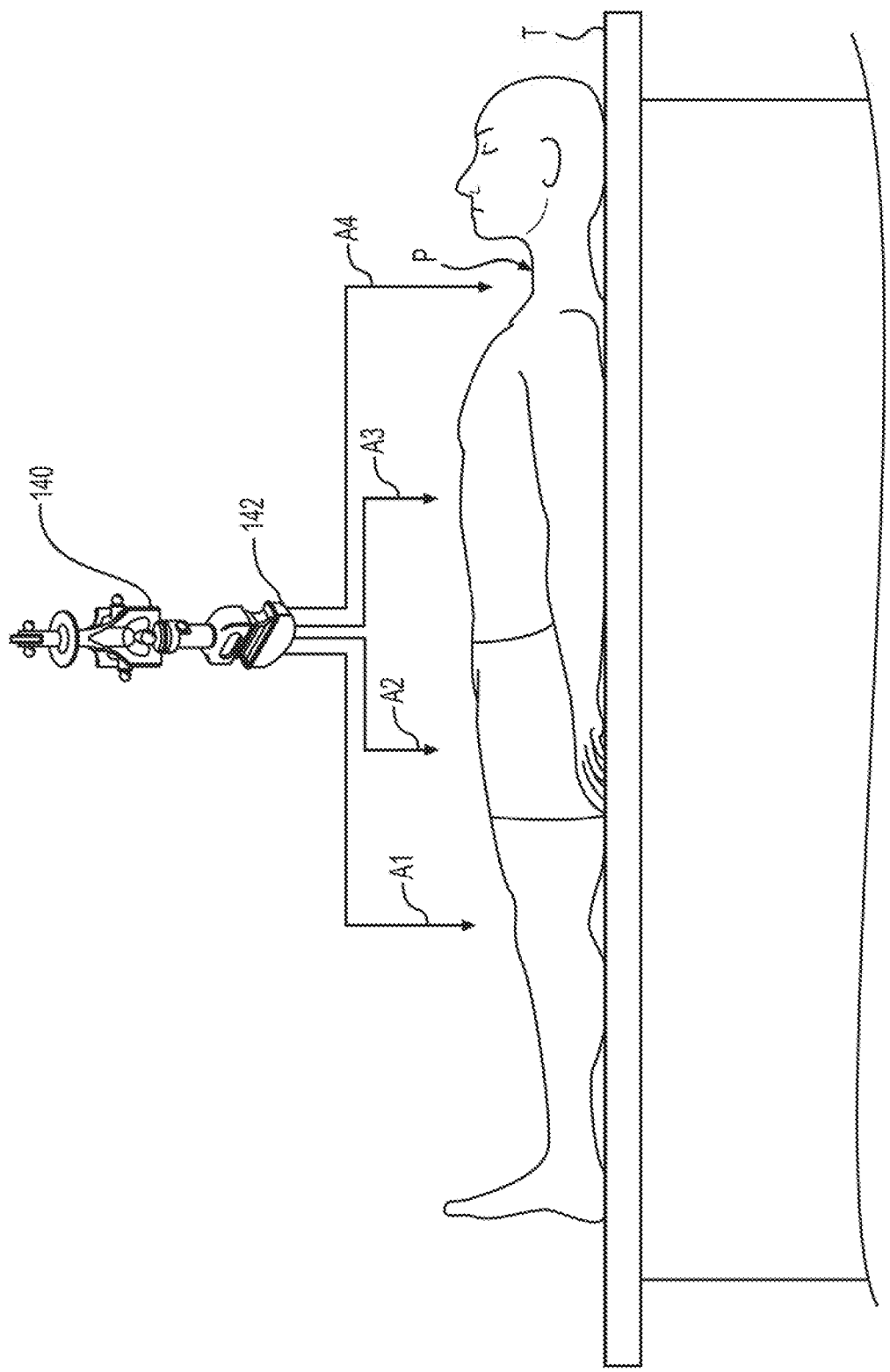
FIG. 2D is an environmental perspective view showing an embodiment of the tissue imaging system of FIGS. 1A and 1B illustrating obtaining ultrasound images in various portions of a body, according to the present invention.

As shown in FIGS. 2B and 2C, the ultrasound probe 142 is being used for imaging different parts of the patient P body at locations L2, L3, for example. In addition, FIG. 2D indicates that the system 100 with the ultrasound probe with tracker system 140 can be used for imaging a plurality of different parts of the body at locations or areas A1, A2, A3, A4, for example.

Figure 3:
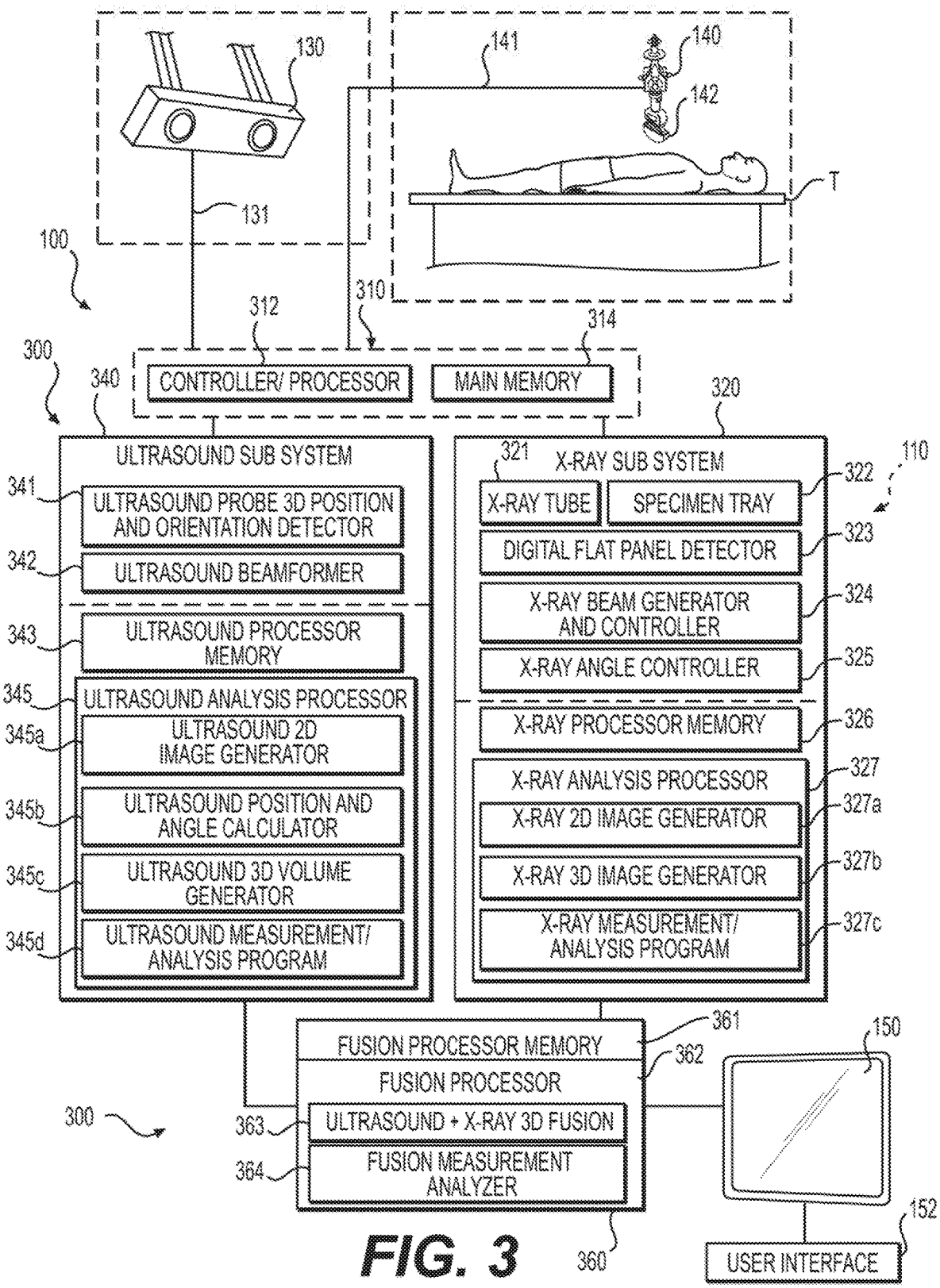
FIG. 3 is a schematic illustration of components of an embodiment of a controller, an ultrasound sub-system and X-ray sub system, and an ultrasound and X-Ray image fusion sub-system of an embodiment of the tissue imaging system of FIGS. 1A and 1B, according to the present invention.

FIG. 3 is the schematic representation of the hardware, firmware and/or software system components 300 of the tissue imaging system 100. The components 300 are integrated with the Image Comparison and Generation System 180, the X-ray controller system 160 and the ultrasound beamformer system 170 for control, imaging, visualization, measurement, comparison and analysis in the generation of the 2D and 3D ultrasound and X-ray images in the system 100 in performing various operations and processes in the image generation in the imaging system 100.

Referring to the system components 300 of FIG. 3, a main control system 310 includes the controller processor 312 and a main memory 314 that controls the ultrasound subsystem 340, an X-Ray subsystem 320, an Image Fusion generator 360, and a user interface 152. The ultrasound subsystem 340 includes the hardware, firmware and/or software components for ultrasound based tissue imaging. An ultrasound probe 3D position and orientation detector 341 connects to the Infrared 3D Imaging Camera 130 to determine the position and orientation of the 3D markers on the ultrasound probe with tracker system 140. An Ultrasound beamformer 342 controls and reads the data from the ultrasound probe 142 to generate 2D ultrasound images via the ultrasound 2D image generator 345a. The ultrasound beamformer 342 can be a suitable commercially available beamformer, such as, for example, an HBU Beamformer Board, Sonoscanner, Paris, France. An ultrasound processor memory 343 stores the 2D images, and the position and orientation information that is used by an ultrasound analysis processor 345. An ultrasound 3D volume generator 345c uses the 2D ultrasound images and an ultrasound probe position and orientation (angle) calculator 345b to generate 3D volume of the ultrasound images and the 3D tumor volume. An ultrasound measurement and analysis program 345d provides tools to contour the 2D ultrasound images to mark the tumor, and perform measurements. The x-ray subsystem 320 contains the hardware, firmware and/or software components required for tissue specimen (for example lumpectomy) and biopsy specimen imaging The x-ray tube 321 generates the x-rays as per the settings specified by an x-ray beam generator and controller 324. The digital flat panel detector system 323 receives the x-rays that pass through the specimen SP placed in a specimen tray 322, 328, generates the x-ray image, and stores it in an x-ray processor memory 326 to be used by an x-ray analysis processor 327 for further processing and analysis. An x-ray angle controller 325 controls the rotational angle in of the x-ray chamber 120 to allow for 360° rotation for imaging the tissue specimen SP from different angles. X-ray imaging of the specimen SP from each angle is used by an x-ray 2D image generator 327a to generate a 2D image of the specimen SP. The plurality of these 2D x-ray images generated from different angles are used by an x-ray 3D image, generator 327b to generate 3D volume of the specimen SP. An x-ray measurement/analysis program 327c uses the 2D and 3D volume data of the x-ray to provide length [X] 1151, width [Z] 1153, height [Y] 1152 and volume 1154 information of the specimen SP imaged by the x-ray system (see, FIG. 11). An image fusion generator 360 contains a fusion processor memory 361 and a fusion processor 362 that stores and processes the 3D volumes of the ultrasound and x-ray. An ultrasound + x-ray 3D fusion 363 module creates the fusion of the 3D volumes of ultrasound and x-ray images and a fusion measurement analyzer 364 calculates or determines the difference in the two volumes. The user interface 152 in conjunction with the interface display 150 provides controls to the user to control the imaging system 100 and displays the required information as described in FIGS. 11, 12A, 12B, 15A, 15B, 18A, 18B and 18C.

FIG. 3 illustrates a generalized system 100 and the above described system components 300 for control, imaging, visualization, measurement, comparison and analysis in the generation of the 2D and 3D ultrasound and X-ray images in the system 100, although it should be understood that the imaging system 100 and system components 300 can represent, for example, a stand-alone computer, computer terminal, portable computing, device, networked computer or computer terminal, or networked portable device. Data may be entered into the system 100 by the user via any suitable type of user interface 152, and can be stored in computer readable, memories of the system components 300, such as memories 314, 343, 326 and 361, which may be any suitable type of computer readable and programmable memory. Calculations, processing and analysis are performed by the controller/processor 312 or other processors of system components 300 of the system 100, which can be any suitable type of computer processor, and can be displayed to the user on the interface display 150, which can be any suitable type of computer display, for example.

The controller/processor 312 and other processors of the system components 300 can be associated with, or incorporated into, any suitable type of computing device, for example, a personal computer or a programmable logic controller (PLC) or an application specific integrated circuit (ASIC). The interface display 152, the processor components of the system components 300 and the memories of the system components 300, and any associated computer readable media are in communication with one another by any suitable type of data bus or other wired or wireless communication, as is well known in the art.

Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memories of the system components 300, or in place of memories of the system components 300, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Figure 4:
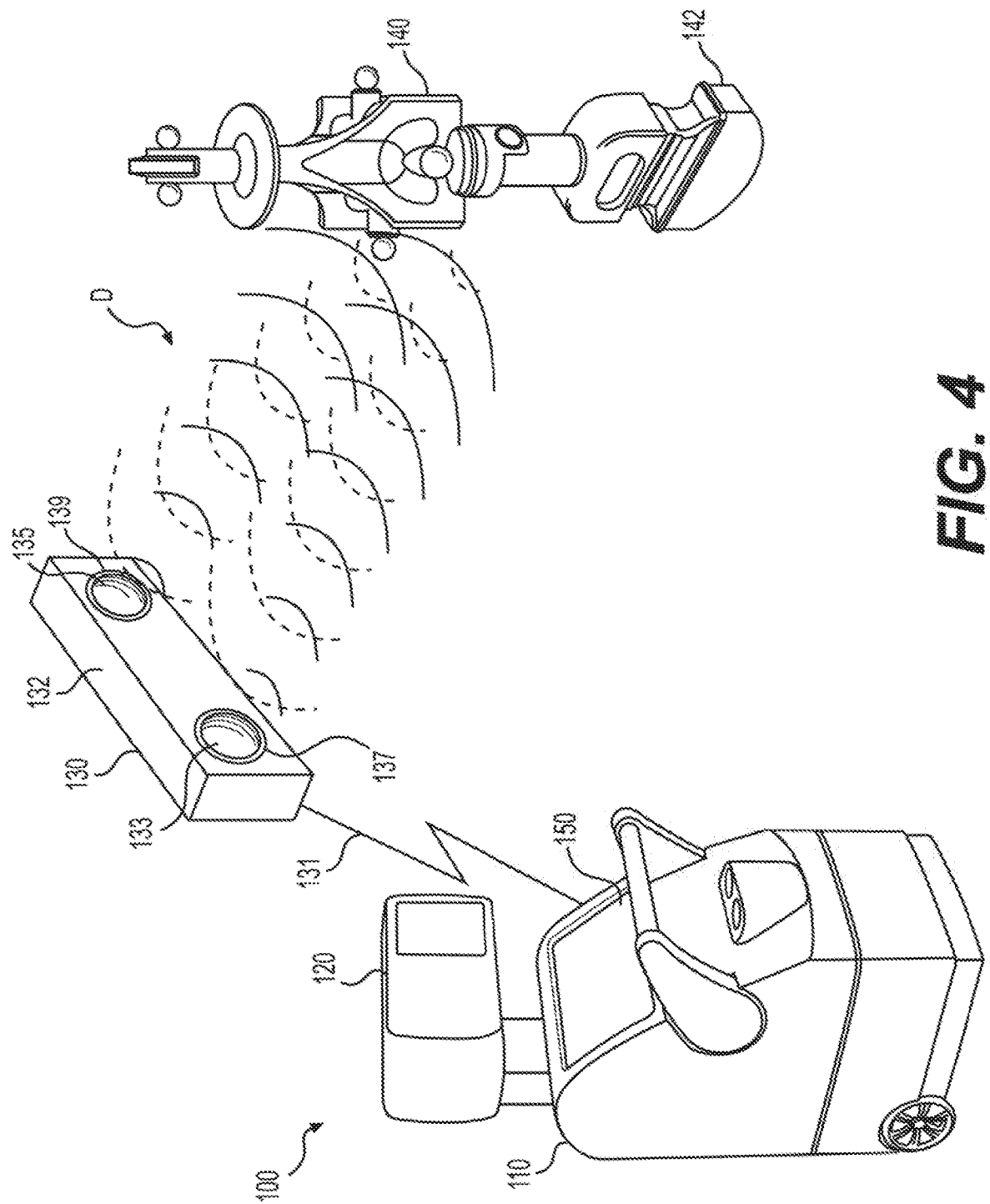
FIG. 4 is a schematic perspective View of an embodiment the tissue imaging system of FIGS. 1A and 1B illustrating tracking position and orientation of an ultrasound probe of the system in obtaining and transmitting ultrasound images of a portion of a body, according to the present invention.

Referring now to FIG. 4, there is illustrated a schematic perspective view of an embodiment the tissue imaging system 100 FIGS. 1A and 1B illustrating tracking position and orientation of the ultrasound probe with tracker system 140 of the imaging system 100 in obtaining and transmitting ultrasound images of a portion of a body according to the present invention.

As illustrated in FIG. 4, embodiments of the present invention advantageously provide the imaging system 100, the infrared 3D Imaging Camera 130, and ultrasound probe with tracker system 140 having the ultrasound probe 142 for tracking a three-dimensional position and an orientation of the tracker system 140, the ultrasound probe 142 obtaining 2D ultrasound images of the tissue or organs in an area of the body of interest. The infrared 3D Imaging Camera 130 can simultaneously detect the three-dimensional position of at least three of the plurality of optical retro-reflective spheres 525 (FIG. 5) indicated by the positional information being detected by the wireless communication "D", and the ultrasound probe 3D position and orientation detector 341 receiving position information from the imaging camera 130 to determine the three-dimensional position and orientation of the optically trackable body 523 (FIG. 6) from the detected three-dimensional position of the optical retro-reflective spheres 525, and thus, the three-dimensional position and orientation of the tracker system 140. The optically trackable body 523 can be connected to ultrasound probe 142 by various suitable connectors known to those skilled in the art to include various movable object mounts, such as movable object mount 675, 667.

Also, the ultrasound probe 142 can include an ultrasonic sensor adapted to locate a three-dimensional position of an area of interest of a body, such as tumor tissue, with respect to a position of the ultrasound probe 142. Desirably, the ultrasound probe 142 includes an ultrasound image generator, such as typically available in a commercially available ultrasound probe such as, for example, PR14 Linear Probe 10-17 MHZ, Sonoscanner, Paris, France. The ultrasound probe 142 can generate two-dimensional ultrasound images of the portion of the patient P containing the area of interest within the body. Such as a person or animal, is on the 243 treatment table T.

The infrared 3D Imaging Camera 130 typically includes a body 132 having a wired or wireless communication with ultrasound sub system 340 in the main body 110 of the imaging system 100. The infrared 3D Imaging Camera 130 has an optical detector body 132 positioned separate and spaced apart from the optically trackable body 523 at a predetermined three-dimensional sensor reference location. The infrared 3D Imaging Camera 130 desirably includes a pair, of separate and spaced apart optical receivers 133, 135, connected to the optical detector body 132, each having a field of view and being adapted to receive optical energy emitted or reflected by each of the plurality of optical retro-reflective spheres 525 when positioned in the field of view typically (centered about the optical receiver pointing angle). The optical receivers 133, 135 detect the three-dimensional sphere position of each of the plurality of retro-reflective spheres 525 when positioned simultaneously within the field of view of both of the optical receivers 133, 135 to produce a plurality of position signals representing the position of such three-dimensional retro-reflective spheres 525. Each of the optical receivers 133, 135, can include a photo-sensitive array (not shown) such as a two-dimensional array charge coupled device CCD sensor or other, similar device, defining a photosensor, to detect optical energy radiated from the retro-reflective spheres 525 when positioned in the field of view of the optical receiver 133, 135. The photosensor provides electrical signals representative of positional information of the retro-reflective spheres 525. Each of the optical receivers 133, 135, also generally includes a lens for focusing the optical energy from the retro-reflective spheres 525 on the photosensor. Also, the infrared 3D imaging Camera 130 can be any of various suitable cameras, as are well-known to those skilled in the art, as, for example, a camera or opti-electrical motion measurement system known as the Polaris®, by Northern Digital Inc., Ontario Canada.

Where the plurality of indicators are in the form of the optical retro-reflective spheres 525, the Infrared 3D imaging Camera 130 can include a pair of infrared illuminators, desirably in the form of a pair of directional infrared illuminator (arrays) 137, 139. The first illuminator 137 is positioned in a surrounding relationship adjacent optical receiver 133 and the second illuminator 139 is positioned adjacent the other optical receiver 135 to selectively illuminate each of the plurality of optical retro-reflective spheres 525 when positioned in the field of view of the respective adjacent optical receiver 133, 135. This provides the requisite optical energy necessary to view the optical retro-reflective spheres 525 within the field of view of the respective adjacent optical receiver 133, 135.

The ultrasound probe 3D position and orientation detector 341 of the ultrasound subsystem 340 is in communication with the infrared 3D Imaging Camera 130 and is responsive to the plurality of position signals produced by the infrared 3D imaging Camera 130 to determine the three-dimensional retro-reflective sphere 525 position of each of the plurality of retro-reflective spheres 525 when positioned simultaneously within the field of view of both of the optical receivers (133, 135) of the infrared 3D Imaging Camera 130. The ultrasound sub-system 340 including ultrasound probe 3D position and orientation detector 341 in conjunction with the controller processor 312 analyzes the two-dimensional position of each sphere 525 in the field of view of both receivers 133, 135, with respect to the position on the photosensor, to determine the three-dimensional location of each sphere 525 simultaneously in the field of view of the receivers 133, 135. The main memory 314 accessible by the controller processor 312 to store a table of definitions containing the segment lengths "S" (FIG. 8) between each pair of the plurality of optical retro-reflective sphere 525.

Figure 8:
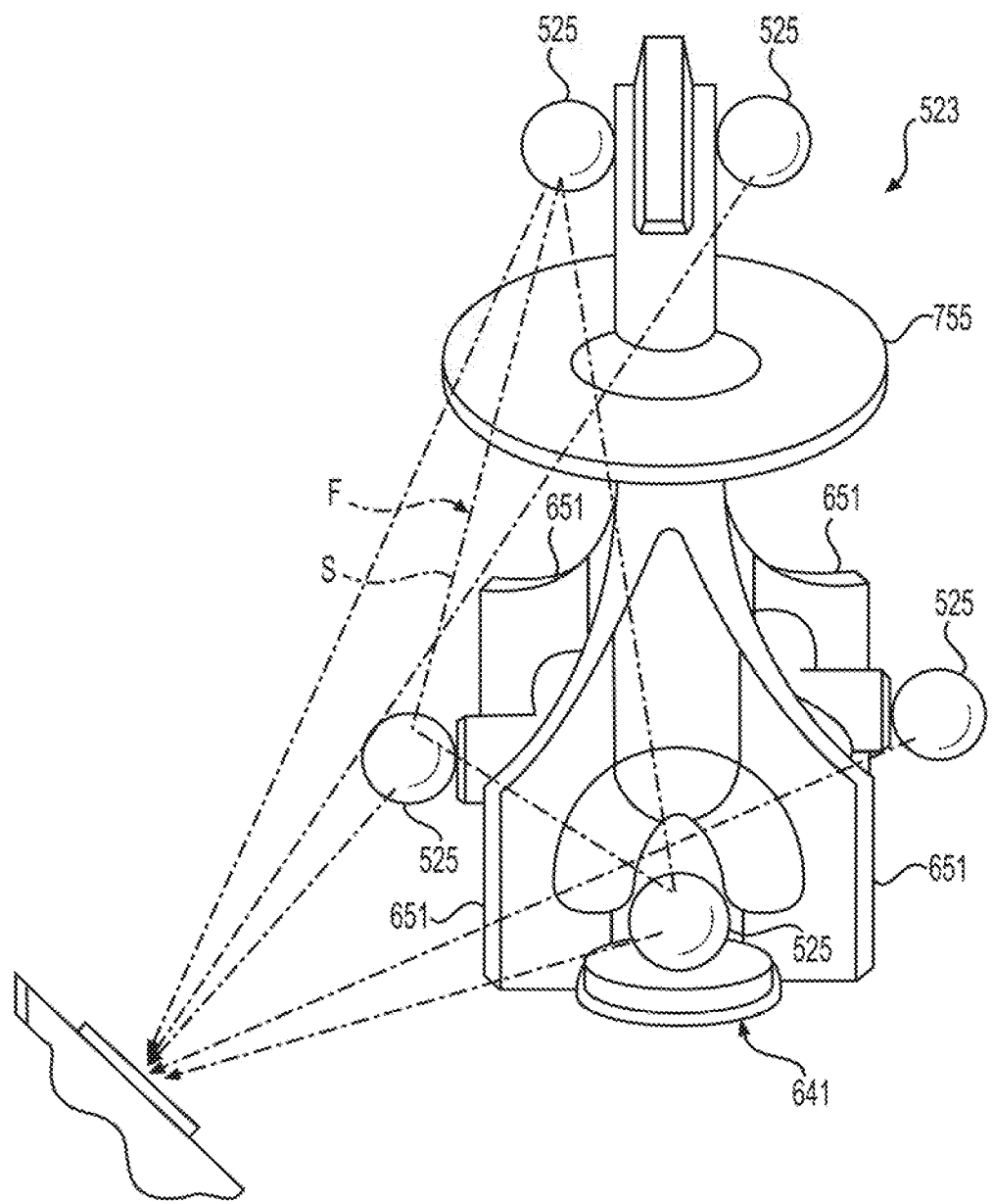
FIG. 8 is a perspective view of an embodiment of an optically trackable body illustrating tracking position and orientation using the optically trackable body in an embodiment of the tissue imaging system of FIGS. 1A and 1B, according to the present invention.

The Infrared 3D Imaging Camera 130 can be used to view the reflective spheres 525 positioned in its field of view, and thus, view at least one of the plurality of geometric figures (FIG. 8). The ultrasound sub-system 340 including ultrasound probe 3D position and orient on detector 341 can then be used to identify which one of the plurality of geometric figures F is positioned in the field of view of the Infrared 3D Imaging Camera 130. A lookup table containing various segment lengths between pair combinations of the retro-reflective spheres 525, or similar collection of data, can be used, as can be stored in the main memory 314, for example.

Responsive to the segment lengths S (FIG. 8) and the three-dimensional location of at least three retro-reflective spheres 525 simultaneously in the field of view of both optical receivers 133, 155, ultrasound sub-system 340 including ultrasound probe 3D position and orientation detector 341 can determine which of the plurality of geometric figures F (FIG. 8) is in view of the optical receivers 133, 135. Once the particular geometric figure F is identified, the ultrasound sub-system 340 including ultrasound probe 3D position and orientation detector 341 by determining the current orientation of the particular geometric figure F, can then further determine the three-dimensional position and the orientation of the optically trackable body 523 of the ultrasound probe with tracker system 140, and thus, the area of interest of a body or patient P. The plurality of retro-reflective spheres 525 are assigned three-dimensional coordinate positions with respect to an origin of a coordinate system assigned to the ultrasound probe with tracker system 140 to provide a reference to the origin and a linear direction of each axes of the assigned coordinate system of the ultrasound probe with tracker system 140. The linear direction of each axes of the assigned coordinate system of the ultrasound probe with tracker system 140 coincide with an orientation of each geometric figure F, and thus, can define the orientation of the ultrasound probe with tracker system 140. Other methodologies of defining orientation, known by those skilled in the art, can also be used as, for example, the orientation could be defined as the longitudinal, lateral, or some other real or user-defined axes of the ultrasound probe with tracker system 140.

The ultrasound sub-system 340 including ultrasound probe 3D position and orientation detector 341 can analyze the position and orientation of the identified geometric figure F in the field of view of the Infrared 3D Imaging Camera 130 which can then be used to determine the position and orientation of the ultrasound probe 142. Specifically, responsive to position signals produced by the Infrared 3D Imaging Camera 130 regarding the retro-reflective spheres 525 in the field of view of the Infrared 3D Imaging Camera 130 and segment lengths S previously stored of a table of definitions stored in the main memory 314, or other associated memory in the components 300, the ultrasound sub-system 340 including ultrasound probe 3D position and orientation detector 341 can determine the three-dimensional position and the orientation (viewing angle) of the ultrasound probe 142.

By continuously analyzing the position and orientation of the geometric figures F, the position and orientation of the ultrasound probe 142 can be continuously re-determined while the geometric figures F remain in the field of view of the Infrared 3D Imaging Camera 130. The position and orientation of the ultrasound probe 142 can be continuously tracked through various rotations of the ultrasound probe 142 by obfuscating a first of the plurality of retro-reflective spheres 525 as it leaves the field of view of the Infrared 3D Imaging Camera 130 to prevent the first of the plurality of retro-reflective spheres 525 from becoming optically coincident with a second of the plurality of retro-reflective spheres 525. This can allow ultrasound sub-system 340 including ultrasound probe 3D position and orientation detector 341, upon determining one of the plurality of geometric figures F is exiting view, to thereby replace the one of the plurality of geometric figures F positioned in the field of view of the Infrared 3D Imaging Camera 130 with another one of the plurality of geometric figures F positioned in the field of view of the Infrared 3D Imaging Camera 130. This second of the plurality of figures F can then continuously be tracked until replaced with a third of the plurality of figures F to provide Continuous tracking, for example.

Figure 5:
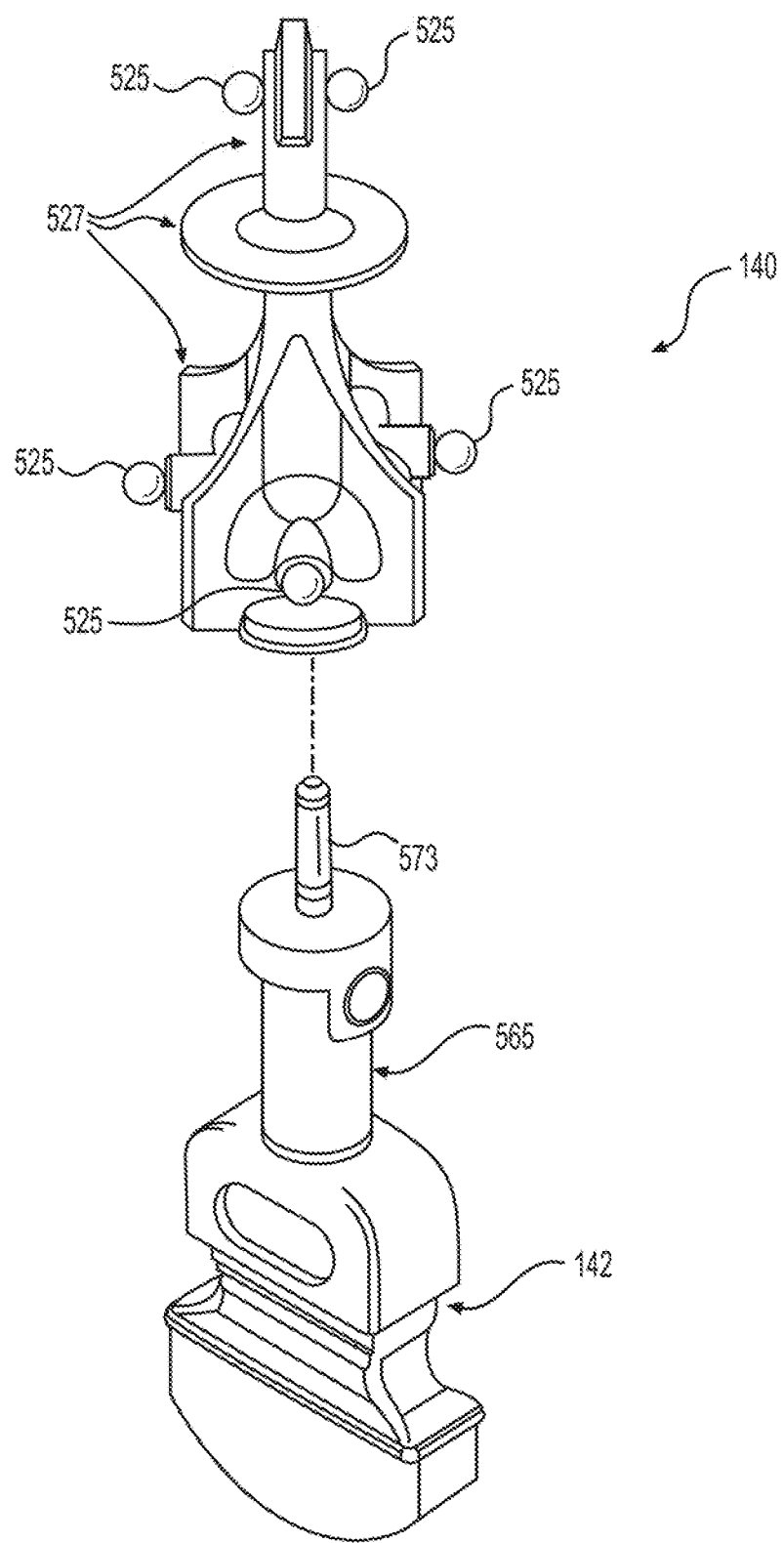
FIG. 5 is an exploded perspective view of an embodiment of an ultrasound probe in an embodiment of a tissue imaging system of FIGS. 1A and 1B, according to the present invention.

Referring now to FIG. 5, there is illustrated an, exploded perspective view of an embodiment of an ultrasound probe with tracker system 149 in an embodiment of the tissue imaging system 100 of FIGS. 1A and 1B according to the present invention.

As mentioned, a plurality of optical indicators, such as optically retro-reflective spheres 525, are connected or mounted to the optically trackable body 523 to form a plurality of desirably dissimilar geometric figures F, such as, for example, as can be seen from FIG. 8. A plurality of obfuscators provided by variously positioned obfuscating flanges 527, obfuscating projections, or other obfuscating obstacles, known to those skilled in the art, optically separate each of the plurality of optical retro-reflective spheres 525 from each other to prevent each of the plurality of retro-reflective spheres 525 from becoming optically coincident with another one of the plurality of retro-reflective spheres 525 when viewed along a viewing path, such as, for example, viewing paths which can extend through adjacent spheres 525. The retro-reflective spheres 525 can be formed of retro-reflective prisms (not shown), as understood by those skilled in the art, that reflect light that strikes them in the exact opposite direction, for example.

The optically trackable body 523 correspondingly includes a plurality of separate and spaced apart indicator mounts 729 (FIG. 7) to connect or mount the optical retro-reflective spheres 525 to the optically trackable body 523. The plurality of optically retro-reflective spheres 525 are adapted to be optically tracked over a subset of possible orientations of the ultrasound probe 142. The plurality of retro-reflective spheres 525 desirably can have a dissimilar preselected segment length S (FIG. 8) between each pair combination. A plurality of combinations of typically at least three of the plurality of retro-reflective spheres 525 can define a plurality of geometric figures F, such as, for example, that geometric figure illustrated in FIG. 8. Further, each sphere 525 in the plurality of the retro-reflective spheres 525 can be positioned to form at least two of the plurality of geometric figures F to reduce a selected number of spheres 525 required, for example.

The three-dimensional location of the retro-reflective spheres 525 and the orientation of each of the geometric figures can provide three-dimensional positional information and orientation information of the optically trackable body 523, and thus, the ultrasound probe 142. Desirably, the geometric figures F are readily distinguishable by the Infrared 3D imaging Camera 130. The plurality of retro-reflective spheres 525 can be positioned such that by the time one of the geometric figures F is no longer visible to the Infrared 3D Imaging Camera 130, another of the plurality of geometric figures F becomes visible to the Infrared 3D Imaging Camera 130. The position and orientation of each identified geometric figure F directly translates to that of the optically trackable body 523, and thus, the ultrasound probe 142.

Although the plurality of indicators can take the form of other locatable indicators, the optical retro-reflective spheres 525 are desirable as they advantageously can negate the requirement for supplying the ultrasound probe with tracker system 140 with electric power or illumination such as that required by indicators in the form of light emitting diodes or fiber optics, for example. Advantageously, this can also reduce the weight and complication of the ultrasound probe with tracker system 140 and can help prevent the ultrasound probe with tracker system 140 from interfering with an operator or the patient P during use of the imaging system 100. Further, the optical retro-reflective spheres 525 are desirable due to their wide field of view which allows detection at a wide range of viewing angles, as can exceed 180 degrees, for example. This can allow for a smaller trackable body 523 with less required spheres 525. Also, associated with the ultrasound probe is a movable object mount 565 as can assist in positioning the ultrasound probe 142. A movable object mounting connector 573 is communicatively associated with the movable object mount 565 for engaging the ultrasound probe 142 with the trackable body 523, for example.

Figure 6:
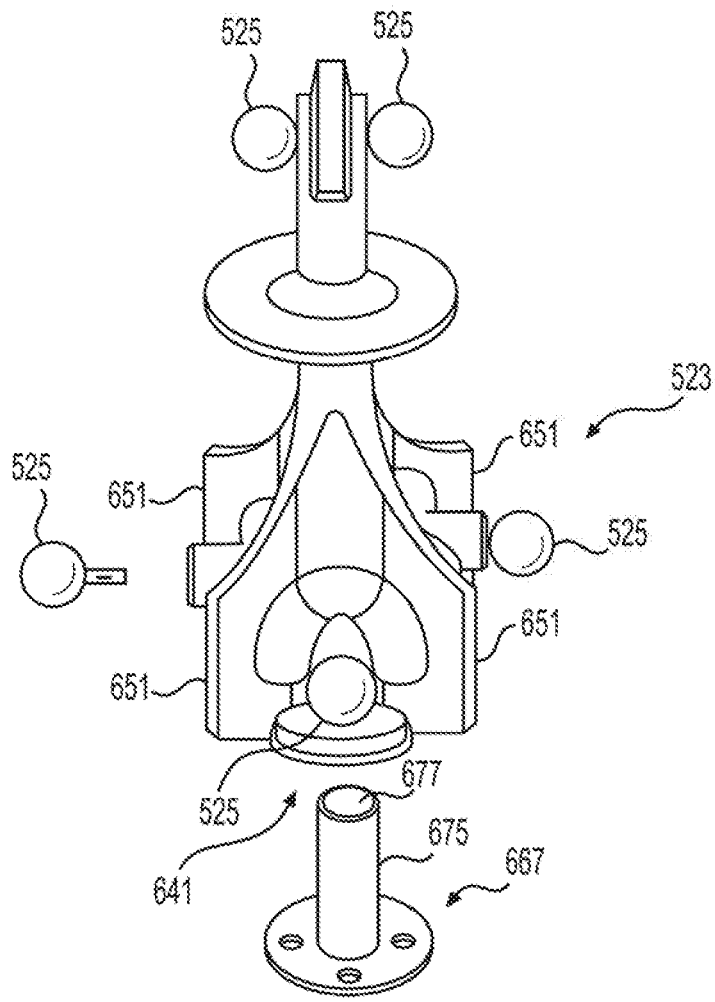
FIG. 6 is an exploded perspective view of an embodiment of an optically trackable body of an ultrasound probe with tracker system for tracking position and orientation in an embodiment of the tissue imaging system of FIGS. 1A and 1B, according to the present invention.
Figure 7:
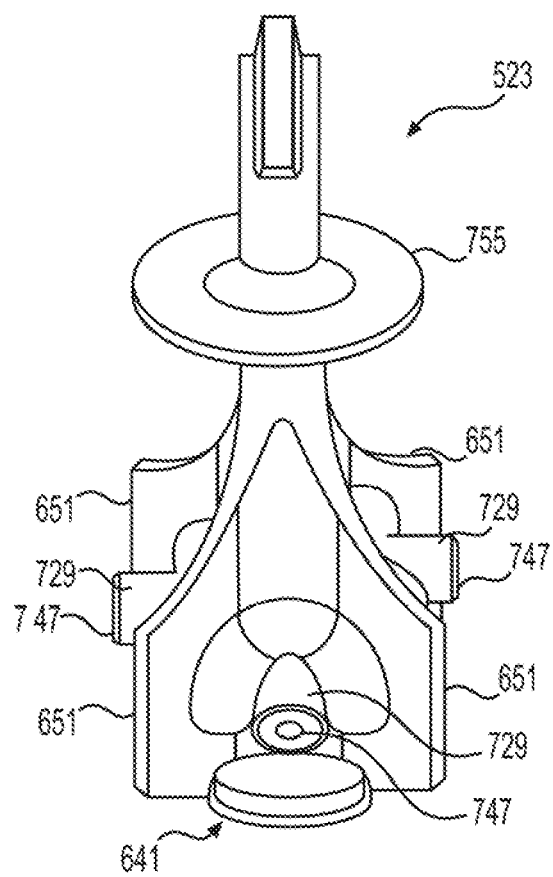
FIG. 7 is perspective view of an embodiment of an optically trackable body of an ultrasound probe with tracker system for tracking position and orientation in an embodiment of the tissue imaging system of FIGS. 1A and 1B, according to the present invention.

Referring now to FIGS. 6, 7 and 8, there are illustrated in FIGS. 6 and 7 exploded perspective views of embodiments of the optically trackable body 523 of the ultrasound probe with tracker system 140 and, in FIG. 8 there is illustrated a perspective view of an embodiment of the optically trackable body 523 of the ultrasound probe with tracker system 140 of a tissue imaging system 100 of FIG. 1A according to the present invention.

As illustrated in FIGS. 6, 7 and 8, the optically trackable body 523 includes a proximal body end portion 641, a distal body end portion opposite the proximal body end portion 641, a medial body portion positioned between and communicatively connected to and extending between the proximal body end portion 641 and distal body end portion. A plurality of indicator mounts 729 on the medial body portion can be equally radially spaced apart but longitudinally staggered in unequal lengths to produce the preselected segment lengths S (FIG. 8). Each of the indicator mounts 729 can include an optical indicator mounting recess 747 or other various forms of fasteners or connectors, known to those skilled in the art, for connecting each respective one of the plurality of spheres 525 or other optical indicators to a corresponding plurality of the indicator mounts 729.

The optically trackable body 523 also includes separating means for optically separating each of the plurality of optical retro-reflective spheres 525 from each other to prevent each of the plurality of retro-reflective spheres 525 from becoming optically coincident with another one of the plurality of retro-reflective spheres 525 when viewed along a viewing path extending directly through either adjacent pair combination of the plurality of retro-reflective spheres 525. This separating means can serve to enhance optical detection of the plurality of retro-reflective spheres 525 to thereby further enhance determination of the positional location and orientation of the optically trackable body 523, and thus, the ultrasound probe 142.

The separating means or separating, members can, include various forms known and understood by those skilled in the art, but are desirably in the form of a plurality of variously shaped and positioned obfuscators including various forms of flanges, projections, separators, attachments, or other types of obstacles can be positioned between a pair of retro-reflective spheres 525. For example, the optically trackable body 523 can include a plurality of longitudinal medial body portion obfuscating flanges 651 sized and positioned substantially parallel to and spaced apart from the longitudinal axis of the medial body portion of the optically trackable body 523. The plurality of medial body portion obfuscating flanges 651 are of sufficient longitudinal length and radial width to optically separate each retro-reflective sphere 525 of the plurality of retro-reflective spheres 525 mounted to the medial body portion of the optically trackable body 523 from each adjacent retro-reflective sphere 525 of the plurality of retro-reflective spheres 525 also mounted to the medial body portion of the optically trackable body 523. This can significantly reduce a possibility of a retro-reflective sphere 525 of the plurality of retro-reflective, spheres 525 mounted to the medial body portion of the optically trackable body 523 from becoming optically coincident with an adjacent retro-reflective sphere 525 of the plurality of retro-reflective spheres 525 also mounted to the medial body portion of the optically trackable body 523, when viewed along a preselected (collinear) viewing path, for example.

Also, the medial body portion obfuscating flanges 651 can be of various geometric designs as long as they are radially short enough so that when observed or viewed such that a reference retro-reflective sphere 525 on the medial body portion of the optically trackable body 523 is "pointing" directly at an observer (e.g. the infrared 3D Imaging Camera 130; FIGS. 4 and 8), the medial body portion obfuscating flanges 651 on either side of the reference retro-reflective sphere 525 do not obscure adjacent retro-reflective spheres 525, but are radially and longitudinally long enough so that when observed such that a reference medial body portion obfuscating flanges 651 is "pointing" directly at the observer, the adjacent obfuscating flanges 651 obscure adjacent retro-reflective spheres 525 positioned "behind" the adjacent obfuscating flanges 651, for example.

Also, the optically trackable body 523 can also include a desirably annular medial body portion obfuscating flange 755 positioned substantially axially parallel with the longitudinal axis of the medial body portion of the optically trackable body 523, such as illustrated in FIG. 8, for example. The radial medial body portion obfuscating flange 755 is positioned and sized to optically separate each retro-reflective sphere 525 of the plurality of retro-reflective spheres 525 mounted to the distal body end portion of the optically trackable body 523 from each adjacent retro-reflective sphere 525 of the plurality of retro-reflective spheres 525 mounted to the medial body portion of the optically trackable body 523. This can prevent each retro-reflective sphere 525 of the plurality of retro-reflective spheres 525 mounted to the distal body portion of the optically trackable body 523 from becoming optically coincident with each retro-reflective sphere 525 of the plurality of retro-reflective spheres 525 mounted to the medial body portion of the optically trackable body 523, when viewed along a preselected viewing path, such as, for example, illustrated in FIG. 8. Also, the radial medial body portion obfuscating flange 755 need not be annular, but can instead be other geometric shapes, as can depend on the use or application, and should not be construed in a limiting sense.

Because the adjacent spheres 525 are effectively prevented from becoming visually coincident with each other of the spheres 525, and thus, prevented from visually interacting with each other with respect to an outside observer, the spheres 525 forming the various different geometric figures are viewable by the Infrared 3D imaging Camera 130 such that the infrared 3D Imaging Camera 130 should generally not find any of the spheres 525 unusable due to coincidence with any of the other spheres 525 in the determination of which of the various different geometric figures F is in the field of view of the Infrared 3D Imaging Camera 130. However, more than one different geometric figure F can be in the field of view, although normally only one would be selected, for example.

Also, the optically trackable body 523 can also include an interior mount recess inwardly extending from the proximal body end portion 641 into the medial body portion as can be used to connect the optically trackable body 523 to the ultrasound probe 142, as described (FIG. 5). The interior mount recess is adapted to slidably receive at least portions of a mounting connector, such as, for example, movable object luting connector 573 (FIG. 5) or a movable object connector 675 of movable object mount 667. Additionally, advantageously mounting connector 675 can include an interior mounting connector recess 677 which can receive the mounting connector 573 (FIG. 5), such that the two mounting connectors 573, 675, can be synergistically implemented together, for example.

Figure 9:
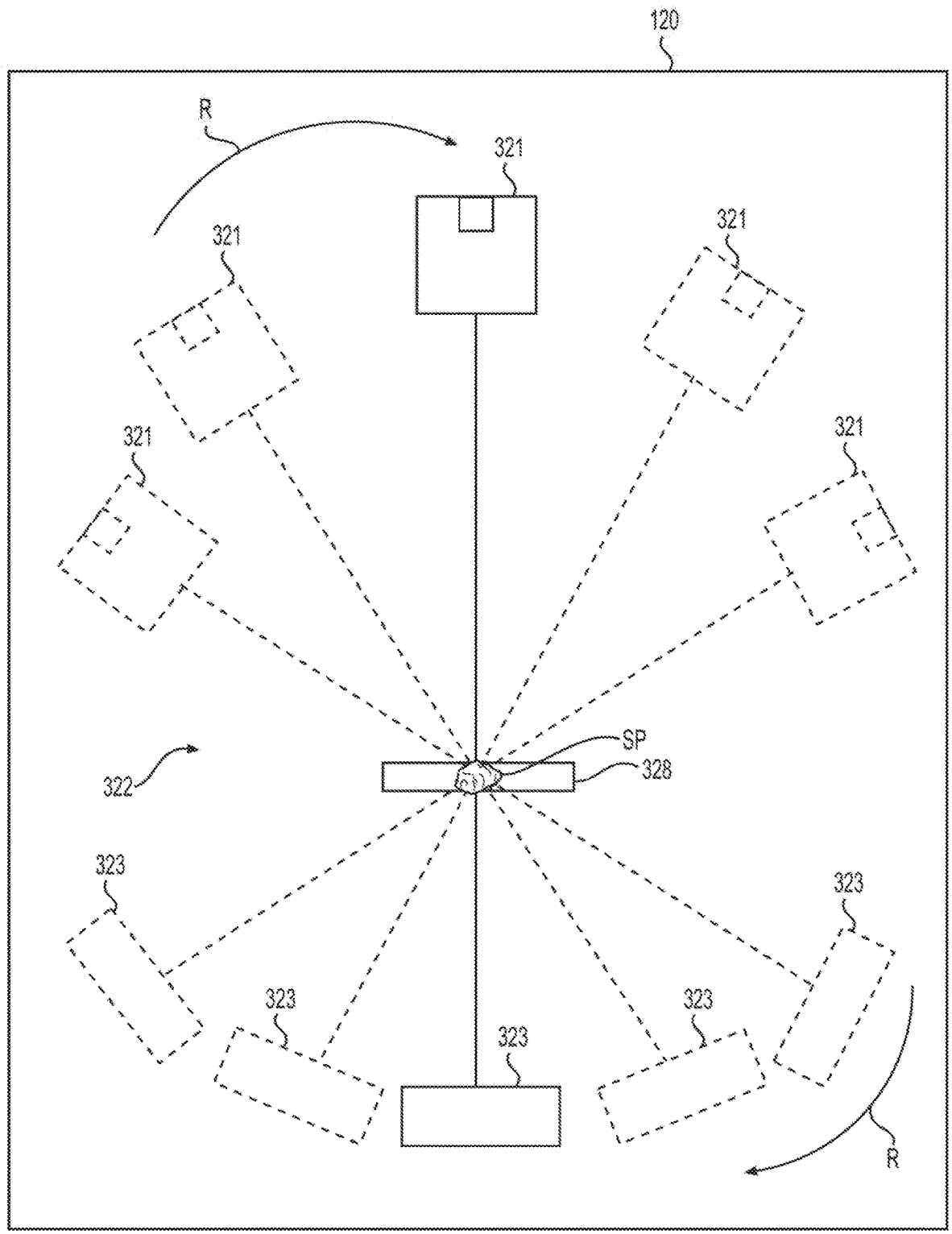
FIG. 9 is a schematic illustration of an embodiment of an X-ray chamber in an embodiment of the tissue imaging system of FIG. 1A, according to the present invention.
Figure 10:
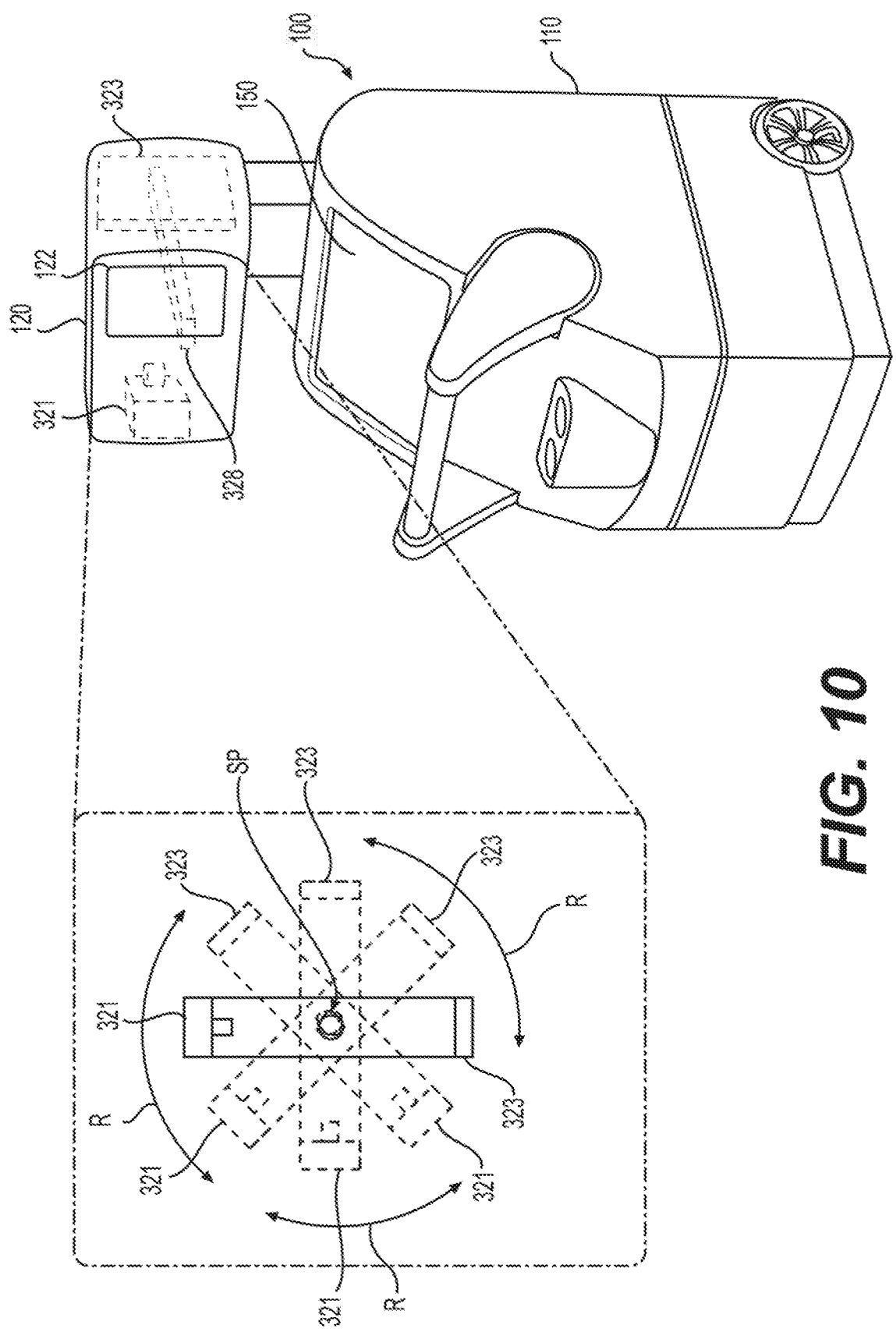
FIG. 10 is a perspective view of an embodiment of the tissue imaging system of FIGS. 1A and 1B conjunction with a schematic illustration of an embodiment of an X-ray chamber of the tissue imaging system, according to the present invention.

FIGS. 9 and 10 are the schematic representation of the angular rotation R of the x-ray chamber 120 in 360°. The x-ray tube 321 and the digital flat panel detector 323 are housed diametrically opposite to each other with the specimen tray 328 in between them. During the rotation of the x-ray chamber 120, the specimen tray 328 remains stationary and the x-ray tube 321 and the digital flat panel detector 323 rotate around it. As the rotation happens, the x-rays are generated by the x-ray tube 321 and as they pass through the specimen SP on the specimen tray 328, these x-rays are detected by the digital flat panel detector 323. The specimen SP to be imaged is placed onto the specimen tray 328 through the door 122 on the x-ray chamber 120 as shown in FIG. 10.

Figure 11:
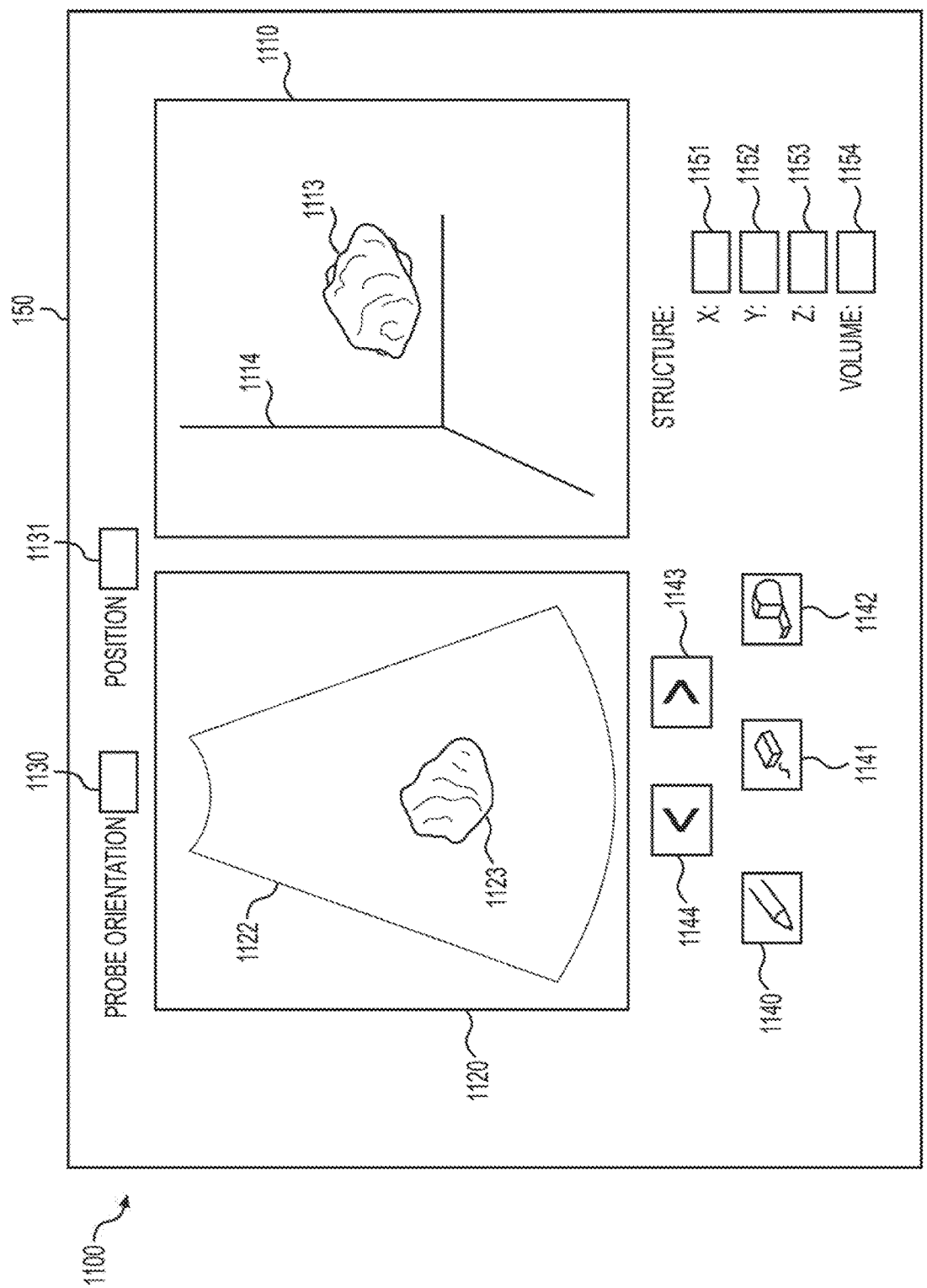
FIG. 11 is a schematic illustration of an embodiment of an interface display illustrating a sub-display of a generated 2D ultrasound image of a contoured tissue portion for removal from a body and a sub-display of a generated 3D X-ray image of the contoured tissue portion for removal from the body in an embodiment of the tissue imaging system of FIGS. 1A and 1B, according to the present invention.

The interface display 150 and its display components during ultrasound imaging of the tissue of interest, such as an organ of interest, is shown in FIG. 11. A live ultrasound display window 1120 shows the live ultrasound image as the patient's P's area of interest is being scanned. The probe orientation 1130 in degrees and the probe position 1131 in x, y, and z coordinate system are displayed for the specific live ultrasound image 1122. The user is provided tools to draw 1140 and erase 1141 the contours in the area of interest (for example: a tumor) 1123. A measurement tool 1142 allows the user to perform measurements on the 2D ultrasound image. The display allows the user to review the scanned ultrasound images using the left arrow 1144 and the right arrow 1143 buttons. A 3D volume of the ultrasound is displayed in display window 1110 along with the contoured structures 1113. The measurements of the structure that includes the length [X] 1151, width [Z] 1153, height [Y] 1152, and volume 1154 are displayed to the user. A 3D axis 1114 is provided that can help in visualization of the orientation of the structure 1113.

Figure 12A:
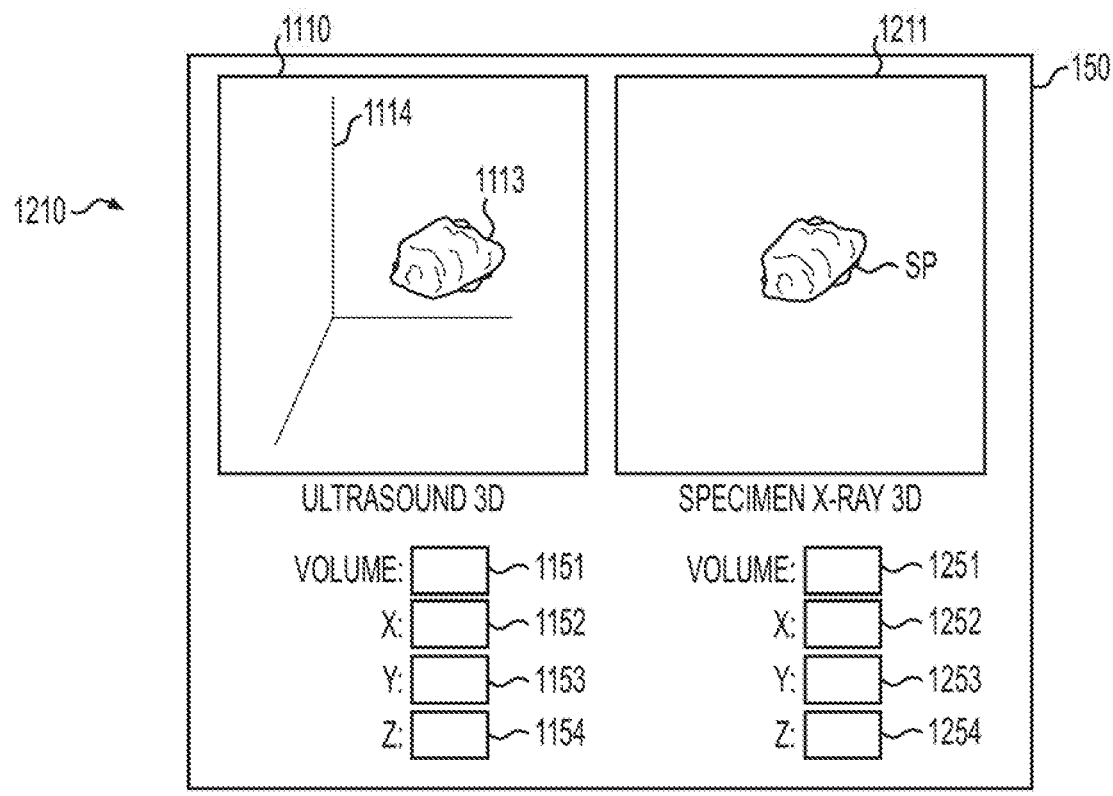
FIG. 12A is a schematic illustration of an embodiment of an interface display illustrating a sub-display of the generated 3D ultrasound image of the contoured tissue portion for removal from the body of FIG. 11 and a sub-display of a generated 3D X-ray image of a tissue specimen removed from the body in an embodiment of the tissue imaging system of FIGS. 1A and 1B, according to the present invention.

Once the tissue specimen SP (for example: a tumor) is extracted from the patient P, and imaged in the x-ray chamber 120, the comparison of the 3D volume image of the extracted specimen SP and the 3D ultrasound based contoured structure 1113 are displayed for comparison as shown in FIGS. 12A and 1B. A volume comparison window 1210 in FIG. 12A shows the side-by-side comparison of the contoured 3D ultrasound structure 1113 in the display window 1110 illustrating the tissue of interest in the body and the extracted specimen SP illustrated in an X-ray 3D volume image displayed in a window 1211. FIG. 12A also displays a volume 1151, a length [X] 1152, a width [Z] 1154, and a height [Y] 1153 of the contoured 3D ultrasound structure 1113 tissue of interest in the body. FIG. 12A also displays a volume 1251, a length [X] 1252, a width [Z] 1254, and a height [Y] 1253 of the 3D specimen SP imaged via the x-ray system. A display window 1220 in FIG. 12B displays an image illustrating the fused contoured ultrasound 3D structure 1113 and the extracted tissue specimen SP imaged via the X-ray system superimposed as a fused image 1223 in a fusion window 1221. A difference in a volume 1261, a length [X] 1262, a width [Z] 1264, and a height [Y] 1263 between the contoured ultrasound 3D structure 1113 and the extracted tissue specimen SP is displayed to the user.

Figure 15A:
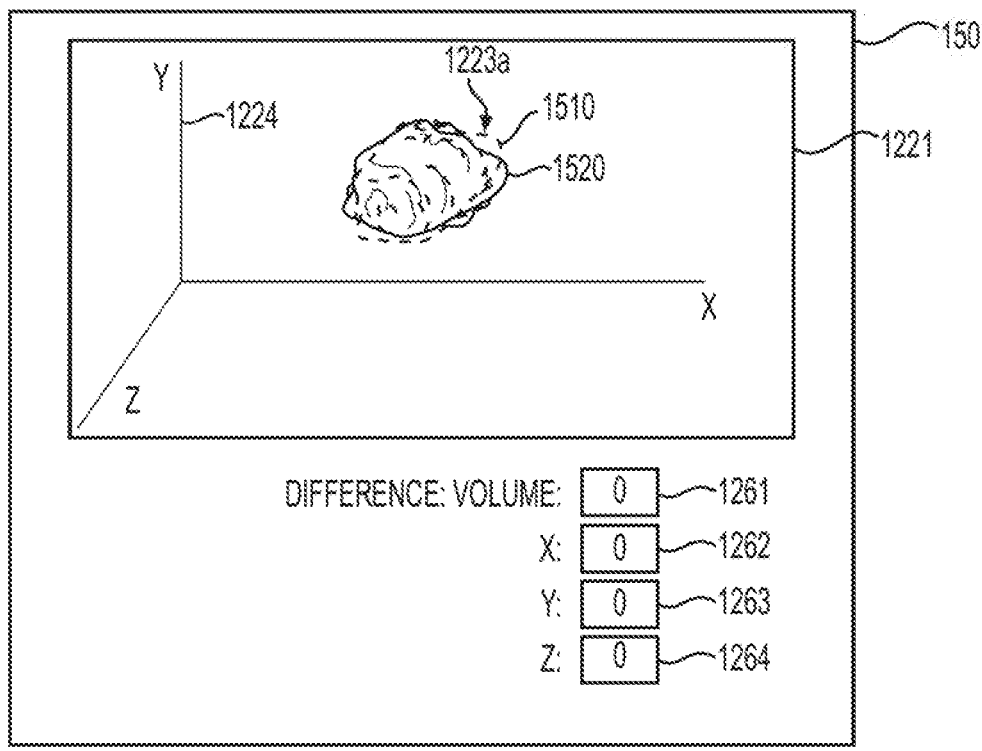
FIG. 15A is a schematic illustration of an embodiment of an interface display illustrating a sub-display of the generated 3D ultrasound image of a contoured tissue portion for removal from the body superimposed upon a generated 3D X-ray image of the tissue specimen removed from a body illustrating where the difference volume indicates there is no substantial difference in volume between the contoured tissue portion for removal from the body and the tissue specimen removed from the body in an embodiment of the tissue imaging system of FIGS. 1A and 1B, according to the present invention.
Figure 15B:
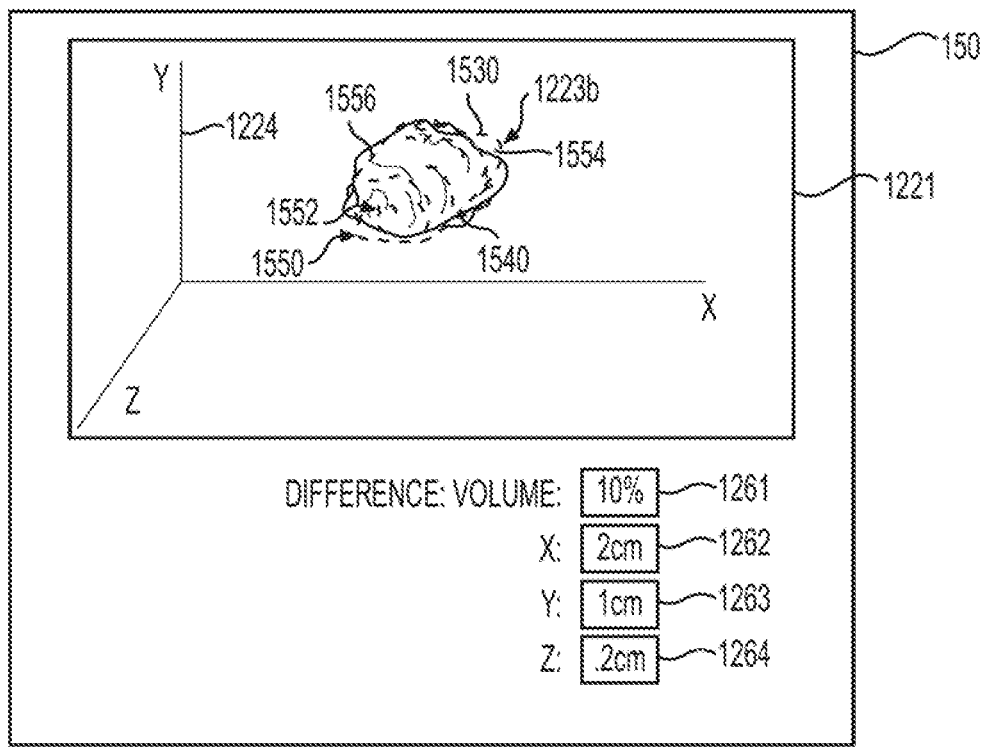
FIG. 15B is a schematic illustration of an embodiment of an interface display illustrating a sub-display of the generated 3D ultrasound image of a contoured tissue portion for removal from the body superimposed upon a generated 3D X-ray image of the tissue specimen removed from a body illustrating where the difference volume indicates there is a difference in volume between the contoured tissue portion for removal from the body and the tissue specimen removed from the body in an embodiment of the tissue imaging system of FIGS. 1A and 1B, according to the present invention.

FIGS. 15A and 15B are examples of the fusion analysis. FIG. 15A shows a fused structure image 1223a with 1510 indicating the ultrasound volume of the contoured ultrasound 3D structure and 1520 indicating the x-ray volume of the extracted tissue specimen SP. As illustrated in FIG. 15A, the imaging system 100 has determined and illustrates on the interface display 150 that there is no measurable difference in the two volumes 1510 and 1520 as illustrated in the measurements of a difference volume 1261, a length [X] 1262, a height [Y] 1263, and a width [Z] 1264 with respect to the volumes 1510 and 1520 as they are substantially aligned on top of each other. However, in FIG. 15B a difference in the fused volume 1223b between a contoured 3D ultrasound structure 1530 and 3D volume 1540 of an extracted specimen SP imaged via X-ray imaging is visible. Image 1550 shows an overall difference in volume wherein images 1552, 1554, and 1556 show the specific areas of volume differences. The quantitative values of the differences between the contoured 3D ultrasound structure 1530 and the 3D volume 1540 of the extracted specimen SP are also displayed in the interface display 150 as a difference volume 1261, a difference length [X] 1262, a difference width [Z] 1264, and a difference height [Y] 1263.

Figure 13:
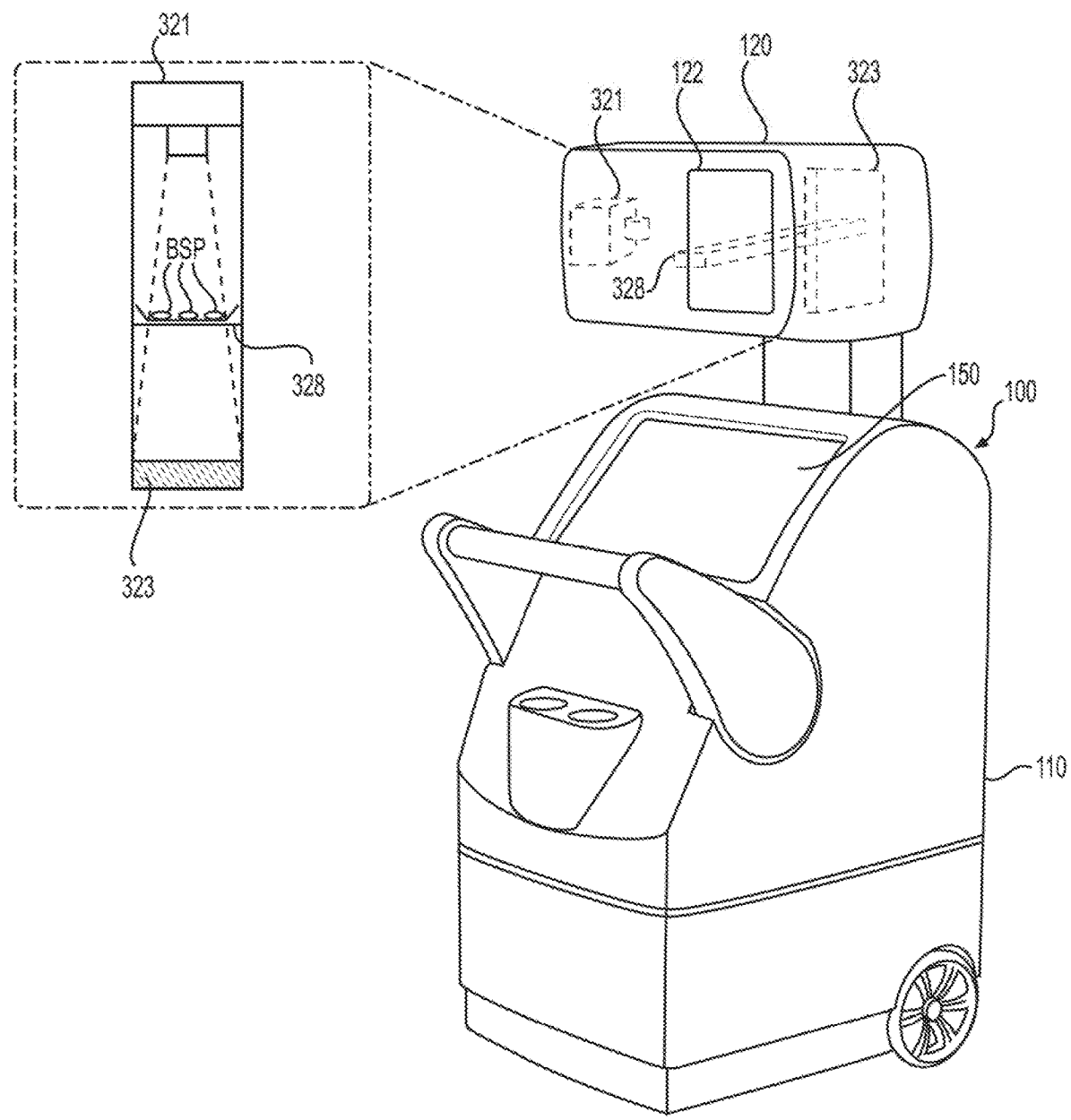
FIG. 13 is a perspective view of an embodiment of the tissue imaging, system of FIGS. 1A and 1B in conjunction with a schematic illustration of an embodiment of an X-ray chamber of the tissue imaging system for tissue biopsy sample imaging, according to the present invention.
Figure 14:
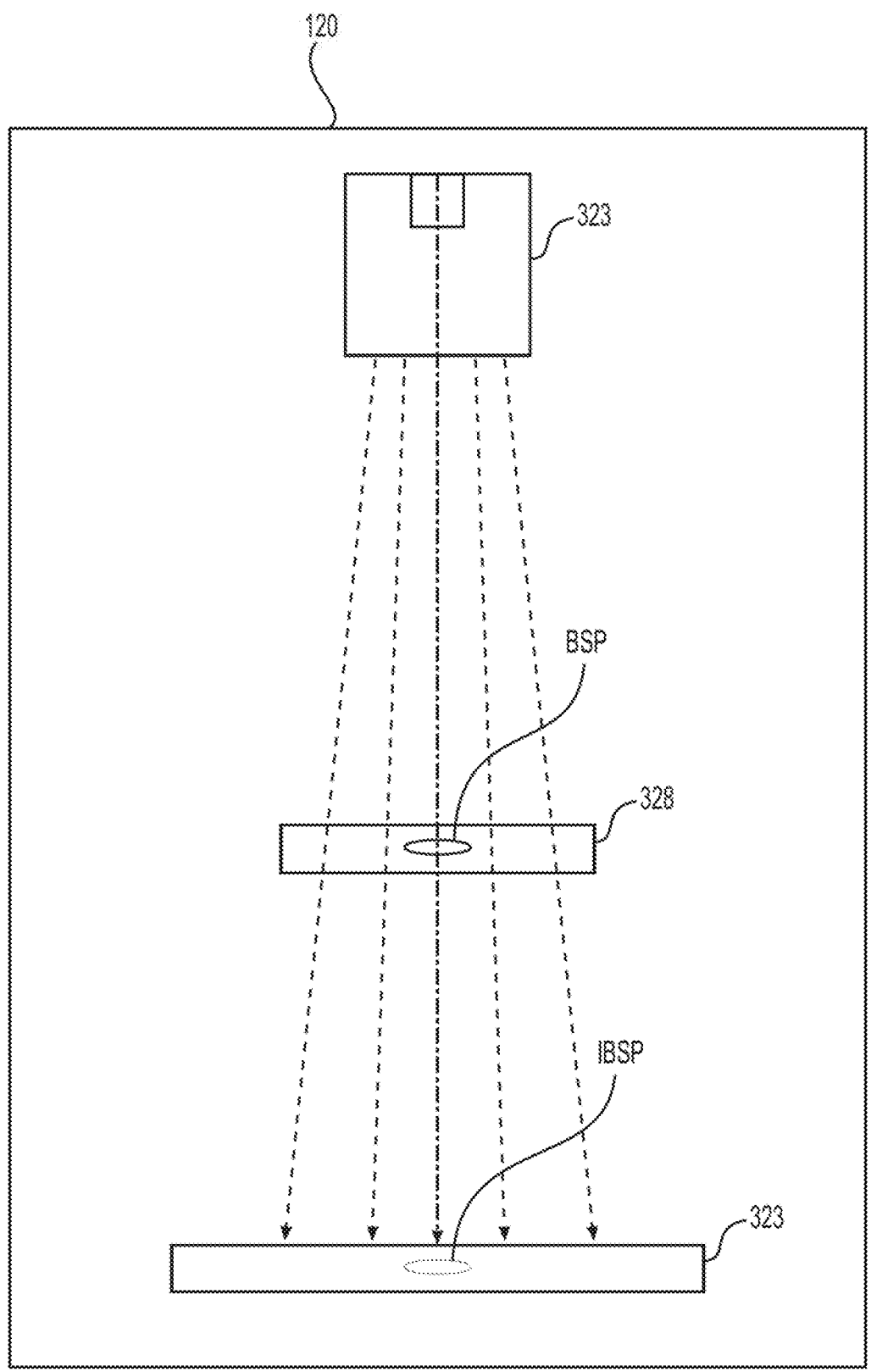
FIG. 14 is a schematic illustration of an embodiment of an X-ray chamber for tissue biopsy imaging in an embodiment of the tissue imaging system of FIGS. 1A and 1B, according to the present invention.

Referencing FIGS. 13 and 14, there is illustrated schematic diagrams of the x-ray system while performing imaging of the biopsy samples, such as to determine if the tissue of interest is to be removed, for example. The biopsy samples are imaged with the x-ray chamber 120 rotated at an angle of 90°. The x-ray tube 321 is positioned over the specimen tray 328 and the digital flat panel detector 323 is positioned below the specimen tray 328, such as illustrated in FIG. 13, for example. The biopsy samples BSP are placed into the specimen tray 328 through the door 122 in the x-ray chamber 120. The x-rays are generated by the x-ray tube 321 and as they pass through the biopsy samples BSP on the specimen tray 328, the x-rays are detected by the digital flat panel detector 323 and a detected image IBSP.

Figure 12B:
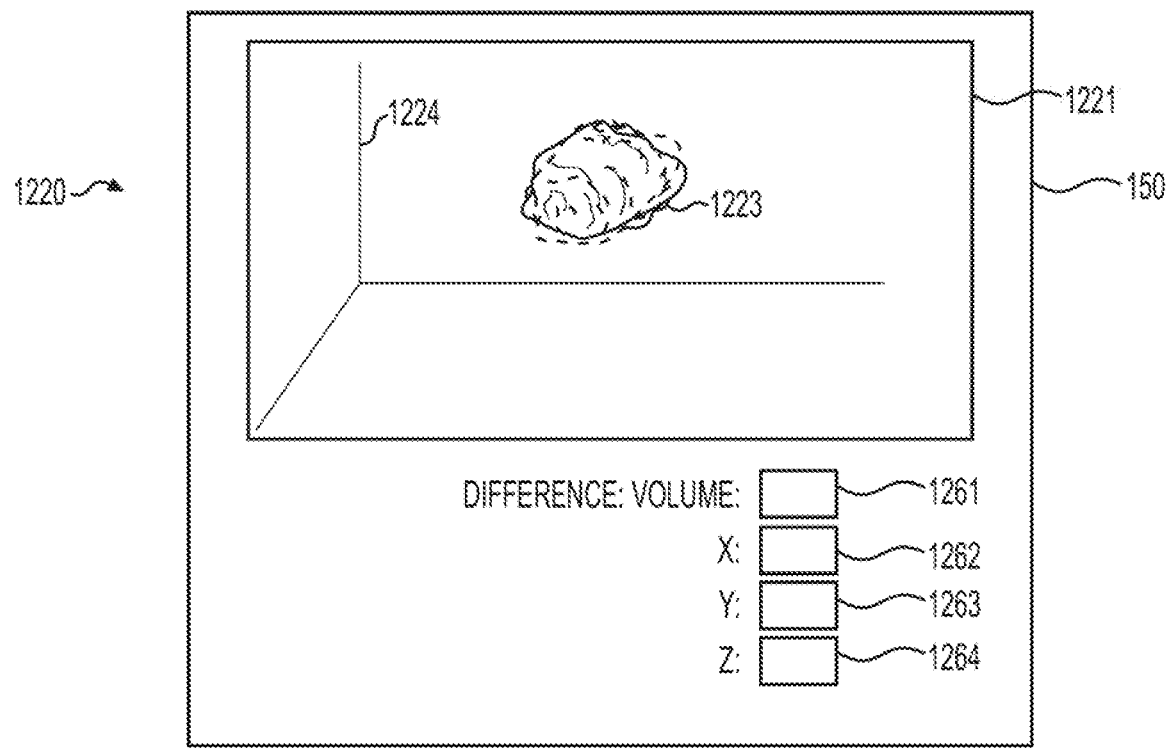
FIG. 12B is a schematic illustration of an embodiment of an interface display illustrating a sub-display of the generated 3D ultrasound image of the contoured tissue portion for removal from the body superimposed upon the generated 3D X-ray image of the tissue specimen removed from a body illustrating a difference volume between the contoured tissue portion for removal from the body and the tissue specimen removed from the body in an embodiment of the tissue imaging system of FIGS. 1A and 1B, according to the present invention.
Figure 16A:
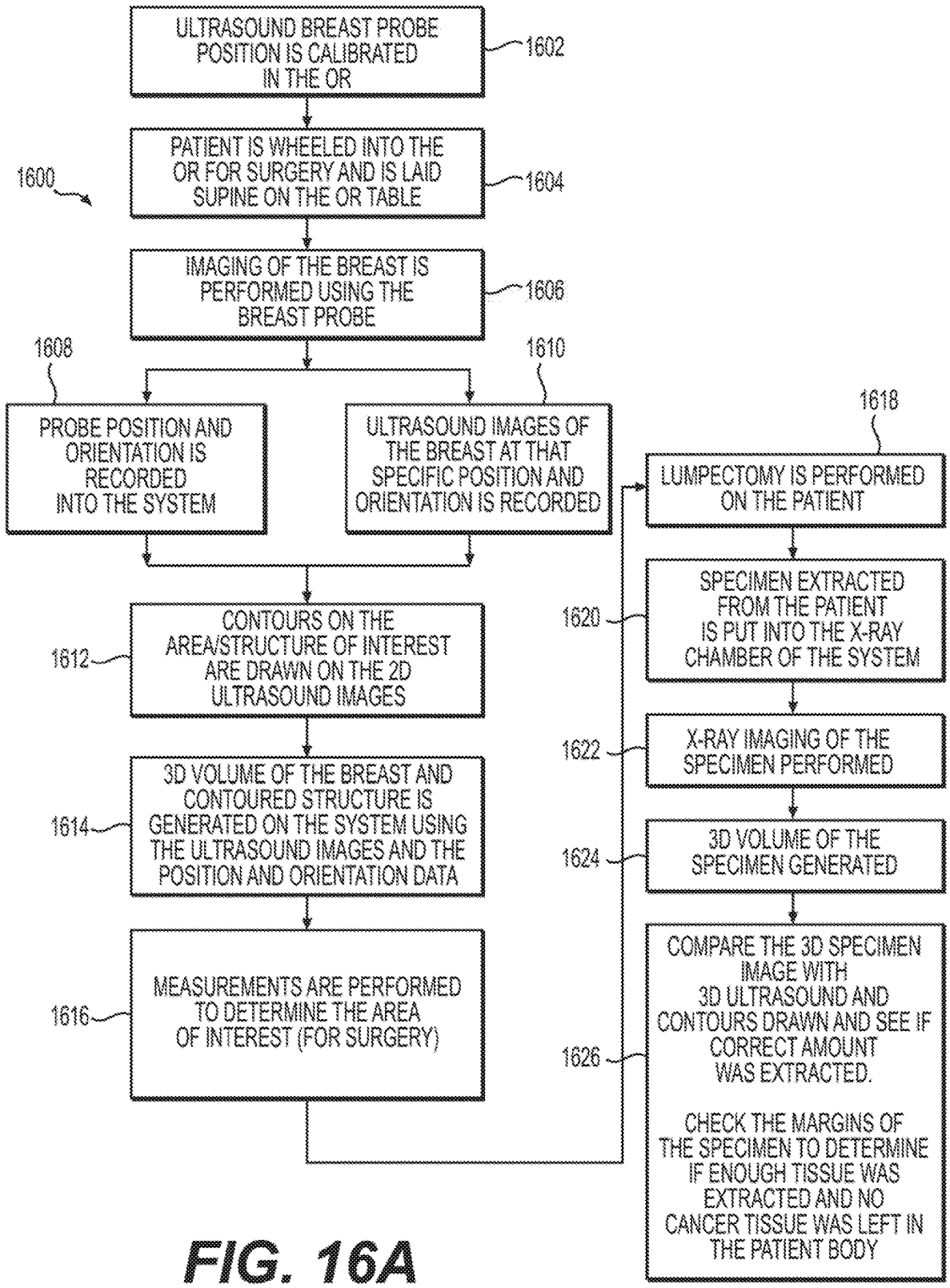
FIG. 16A is an exemplary flow chart for an embodiment of a process for determining a difference volume between a contoured tissue portion for removal from the body and a tissue specimen removed from the body using 3D generated. X-ray and 3D generated ultrasound images in conjunction with an embodiment of the tissue imaging system of FIGS. 1A and 1B, according to the present invention.
Figure 16B:
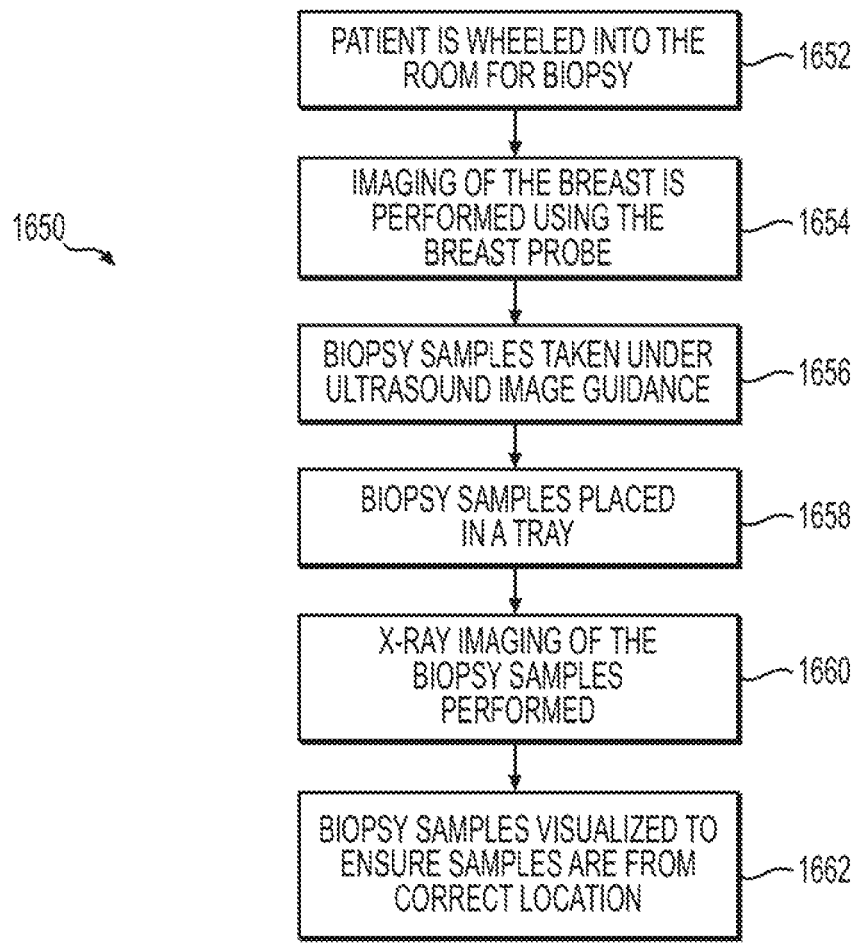
FIG. 16B is an exemplary flow chart for an embodiment of a process for generating X-ray imaging of a biopsy tissue sample in conjunction with an embodiment of the tissue imaging system of FIGS. 1A and 1B, according to the present invention.
Figure 17:
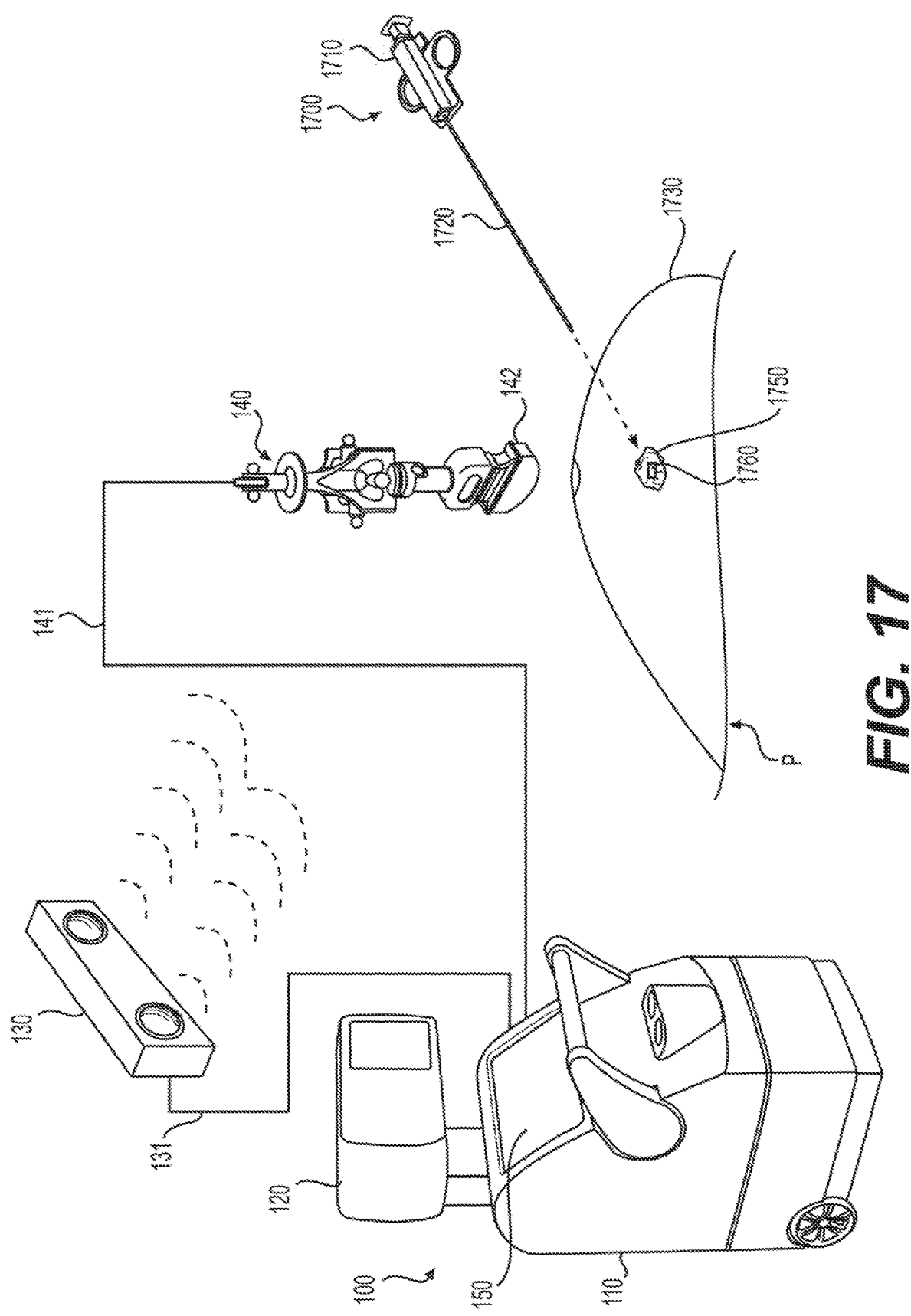
FIG. 17 is perspective view of an embodiment of the tissue imaging system of FIGS. 1A and 1B illustrating using ultrasound imaging for placement of one or more radioactive markers in tissue in a portion of a body for localization, according to the present invention.

As an example of an embodiment of a process for imaging a specimen SP using the imaging system 100 is illustrated by an exemplary process workflow 1600, such as for performing a Lumpectomy, and its analysis is schematically represented in flowchart of the process in FIG. 16A. The first part of the process is Ultrasound Imaging for Tumor Detection: The ultrasound probe with tracker system 140 is connected to the imaging system 100 and is calibrated in the operating room before imaging the patient P as part of step 1602. Patient P is wheeled into the operating room and is laid on the Operating Table T in the supine position in step 1604. The physician images the breast, such as at location L1 (or any other organ or location of interest L2, L3) using the ultrasound probe in the workflow step 1606. Multiple ultrasound images in step 1610 are acquired of the breast using the ultrasound probe 142 in different positions and orientations and the ultrasound probe 142 position and orientation are recorded into the imaging system 100 during step 1608. The physician draws the contours on the tissue of interest, such as a tumor, on the displayed 2D ultrasound images in step 1612, such as of the breast as shown in area of interest 1123. In step 1614, using the position and orientation of the ultrasound image along with the contoured structures, a linear interpolation algorithm, such as known to one skilled in the art, is used to create the 3D volume of the breast and the contoured structures as shown in FIG. 11 in the contoured structures 1113. The imaging system 100 displays on the interface display 150 the measurements of the contoured area of interest, such as a tumor, which is the height [Y] 1152, the length [X] 1151, the width [Z] 1153, and the volume 1154. The second part of the process 1600 is to perform tissue extraction (for example: a Lumpectomy). A surgeon performs a lumpectomy on the patient P in step 1618 and places the specimen SP in the X-ray chamber 120 of the imaging system 100 as part of the workflow step 1620. The third part of the process 1600 is X-Ray Imaging of the specimen SP: In workflow step 1622, x-ray imaging of the specimen SP is performed as described in FIGS. 9 and 10. As the x-ray tube 321 rotates along with the digital flat panel detector 323 around the specimen SP, a 3D volume of the specimen SP is displayed to the physician in the display window 1211 in step 1624, as, for example, by using a back projection algorithm, such as known to one skilled in the art. The fourth part in the process 1600 is the analysis of the specimen SP. In workflow step 1626 a comparison of the contoured structures and the extracted specimen SP is performed to determine if the correct volume for the SP has been extracted. The measurements of the contoured structure 1113 and the specimen SP x-ray volume are displayed as shown in FIG. 12A and the differences in the dimension and volume measurements are displayed as shown in FIG. 12B. The physician then compares and checks the margins of the 3D volumes along with their measurements to determine if enough tissue was extracted. Referring now to FIG. 16B, there is illustrated an process 1650 for a workflow for imaging biopsy samples. In a first step 1652 of the process 1650, the patient P is wheeled into the operating room for biopsy procedure. In a next step 1654, as per the workflow 1900 as described in FIG. 19 and using the imaging system 100 arranged as illustrated in FIG. 17, imaging of the tissue of interest, such as a breast, is performed using the ultrasound probe and tracker system 140. Then, in next step 1656, Biopsy samples BSP from the tissue are extracted under ultrasound guidance. In workflow step 1658, the extracted biopsy samples BSP are placed into the specimen tray 328. Once all the biopsy samples BSP are placed into the specimen tray 328, then in step 1660 the specimen tray 328 is placed into the x-ray chamber 120 and the x-ray imaging is performed as described in FIG. 13 and FIG. 14. In the last step 1662 of the workflow, a needle path as shown in FIG. 18C and the x-ray images of the biopsy samples BSP are visualized to ensure that the biopsies are extracted from the correct location in the body.

Figure 18A:
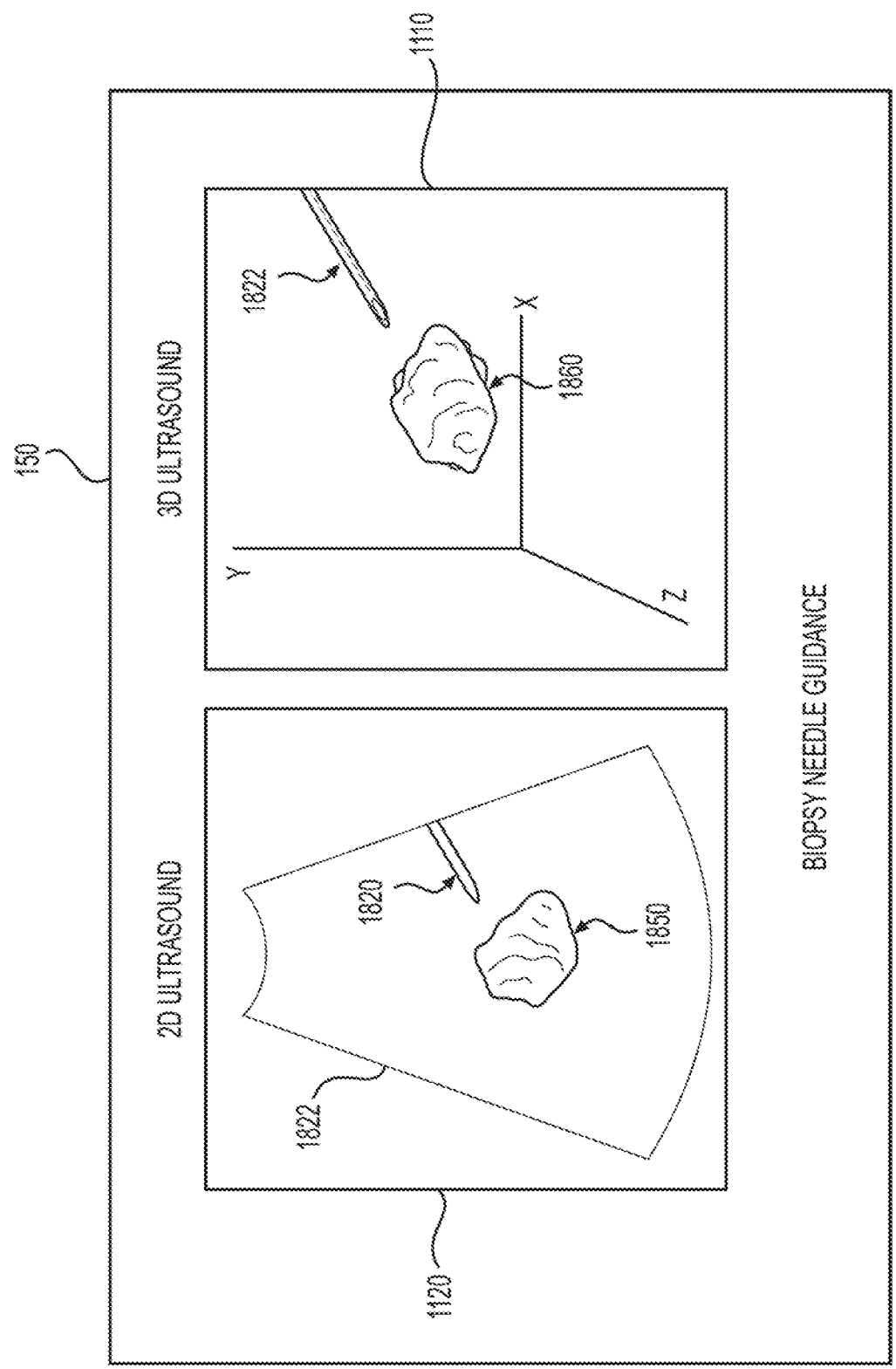
FIG. 18A is a schematic illustration of an embodiment of an interface display illustrating a sub-display of the generated 2D ultrasound image of a tissue portion in a body and a generated 3D ultrasound image of the tissue portion of the body for biopsy needle guidance and placement in an embodiment of the tissue imaging system of FIGS. 1A and 1B, according to the present invention.
Figure 18B:
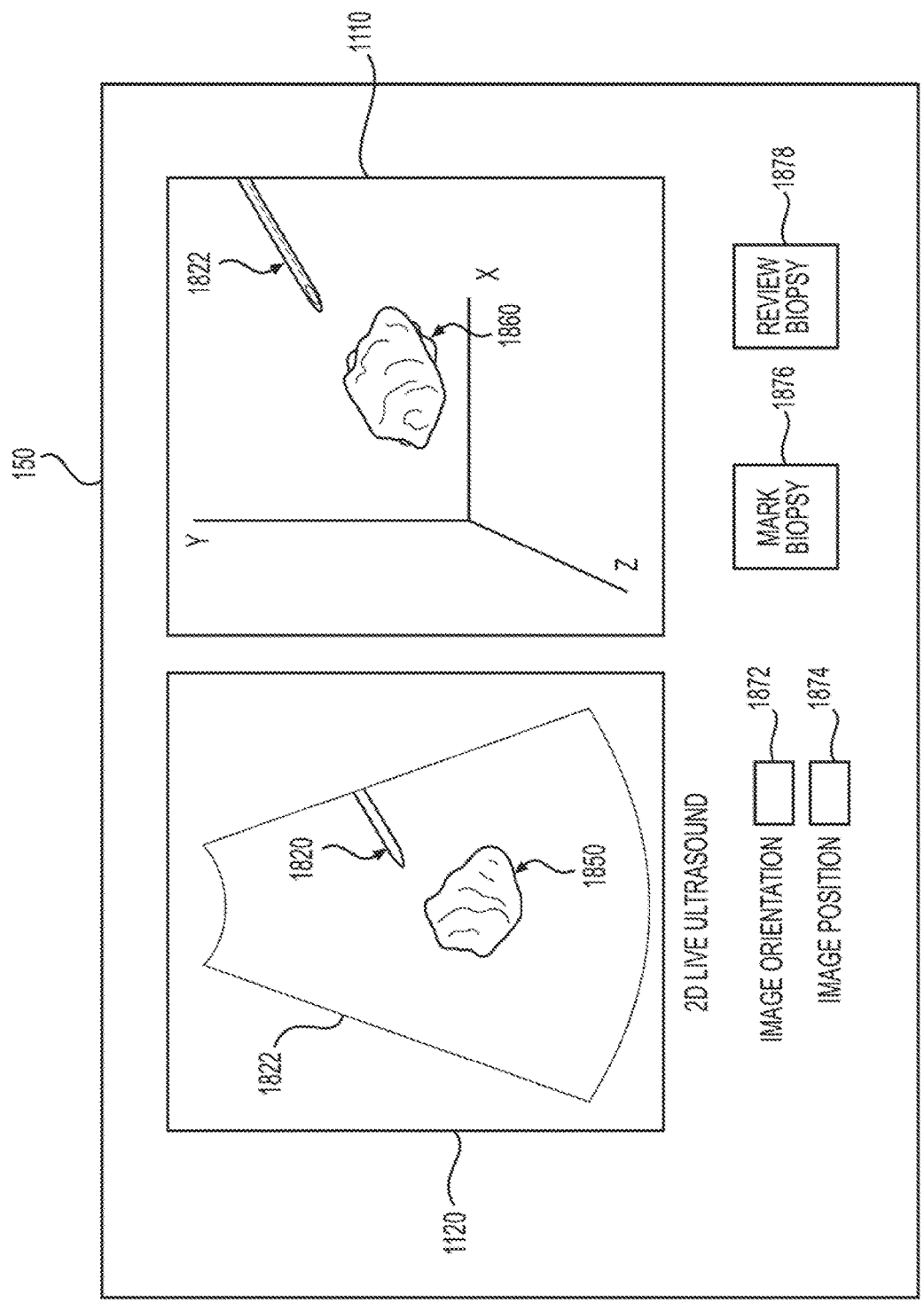
FIG. 18B is a schematic illustration of an embodiment of an interface display illustrating a sub-display of the generated 2D live ultrasound image of a tissue portion in a body and a sub-display of a generated 3D ultrasound image of the tissue portion of the body corresponding to the generated 2D live ultrasound image for biopsy needle guidance and placement and for marking and reviewing the biopsy in an embodiment of the tissue imaging system of FIGS. 1A and 1B, according to the present invention.
Figure 18C:
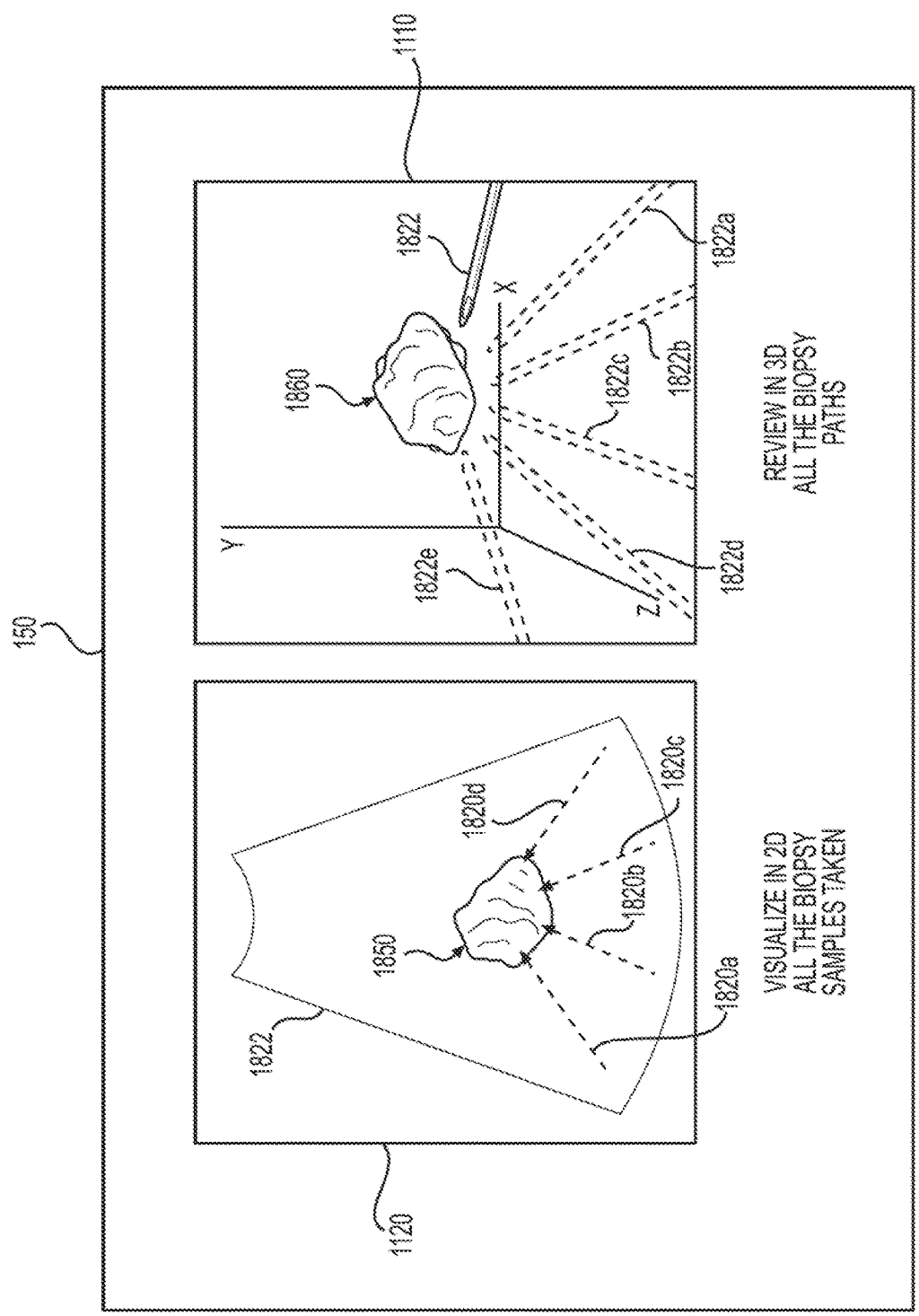
FIG. 18C is a schematic illustration of an embodiment of an interface display illustrating a sub-display of a generated 2D ultrasound image of a plurality of biopsy samples taken of a tissue portion in a body and a sub-display of a generated 3D ultrasound image of the tissue portion of the body corresponding to the generated 2D ultrasound image for a plurality of biopsy paths corresponding to biopsy samples taken of a tissue portion in a body for reviewing a biopsy procedure in an embodiment of the tissue imaging system of FIGS. 1A and 1B, according to the present invention.

Referring to FIGS. 17, 18A and 18B, FIG. 17 is a schematic representation of performing a biopsy or placing a seed marker under ultrasound guidance using the imaging system 100. Ultrasound images of the tissue of interest, such as an organ (for example: the breast), are acquired using the ultrasound probe with the tracking system 140 and the area of interest (for example: a tumor) is contoured and display as contoured image 1850 as, part of an ultrasound image 1822 and a 3D volume 1860 of the contoured structure is created and displayed in the display window 1110 on the interface display 150, as shown in FIG. 18A. A needle system 1700 is a generalized representation of various needle systems that can be used for biopsy or for placing a seed marker 1760 into the area of interest 1750. The needle system 1700 includes a holder 1710 for a needle 1720 and includes the needle 1720. The needle 1720 is inserted into tissue 1730 under ultrasound guidance using the imaging system 100. The needle 1720 that is inserted into the tissue 1730 is displayed in a live ultrasound image 1822 as a needle image 1820 in FIG. 18A. A 3D representation of the needle image is also shown as numeral 1822 in the display window 1110 in FIG. 18A. As the needle 1720 is inserted into the tissue 1730 under ultrasound guidance, the needle image 1820 is displayed along with an image orientation 1872 and an image position 1874 along with the Ultrasound image 1822 as illustrated in FIG. 18B. By clicking on a mark biopsy button 1876 the physician is able to mark the needle path on the needle image 1820 in the ultrasound image display window 1120. Once the needle image 1820 is marked in the 2D ultrasound image, the 3D representation of the needle also indicated by the numeral 1822 is displayed in the 3D window 1110. The physician can mark multiple needle paths as the needle 1720 is inserted into the tissue 1730. To review the needle paths, the physician can click on a review biopsy button 1878 and the images 1120 and 1110 are displayed in the interface display 150 as shown in FIG. 18C. The display 1120 shows 2D ultrasound image 1822 with a plurality of various needle paths, such as needle paths 1820a, 1820b, 1820c, and 1820d. The needle paths are also displayed in 3D as 3D needle paths, such as needle paths 1822a, 1822b, 1822c, 1822d and 1822e, as shown in the display 1110.

Figure 19:
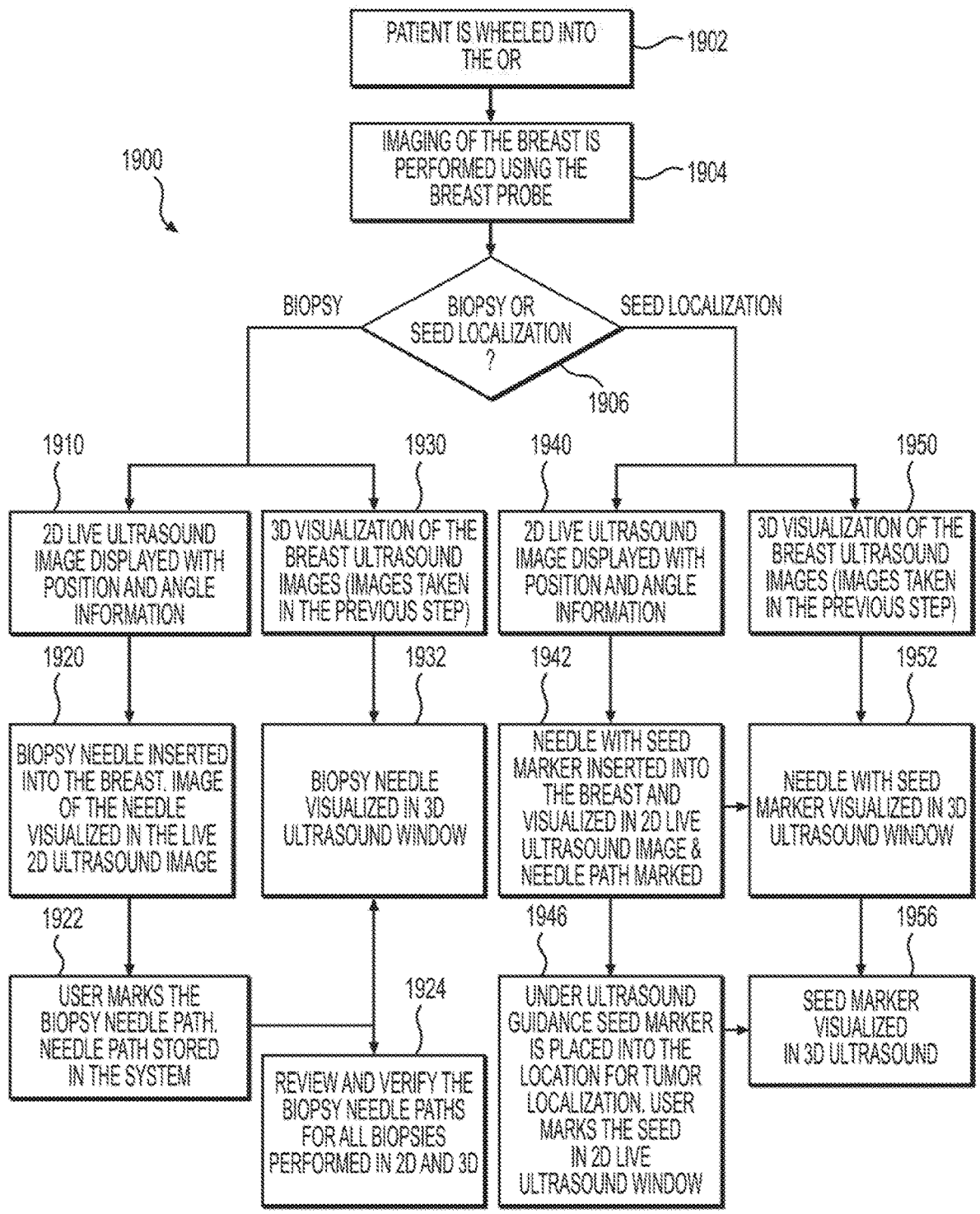
FIG. 19 is an exemplary flow chart for an embodiment of a process for generating 2D and 3D X-ray imaging of a biopsy tissue sample in conjunction with biopsy needle guidance and biopsy procedure review and for visualizing imaging for placement of one or more radioactive markers in tissue in a portion of a body for localization in conjunction with an embodiment of the tissue imaging system of FIGS. 1A and 1B, according to the present invention.

FIG. 19 shows a workflow process 1900 for Biopsy and Seed Localization. As a first step 1902 of the workflow, the patient P is wheeled into the Operating Room. In step 1904 ultrasound imaging of tissue of interest, such as an organ (for example: the breast), is performed using the ultrasound probe with tracker 140. Multiple images of the breast are acquired along with the ultrasound probe position and orientation by the imaging system 100, as previously described. Then, step 1906 is a decision step as part of the workflow process 1900 to decide if a biopsy or a seed marker placement/localization is to be performed. If biopsy is to be performed, the process proceeds to step 1910 and in this step a 2D live ultrasound image of the breast is displayed along with the image orientation 1872 and image position 1874 of the image 1822 as shown in FIG. 18B. In step 1930, a 3D volume 1860 of the ultrasound images acquired in step 1904 is displayed in the display window 1110 as shown in FIG. 18B. Then, in step 1920, the biopsy needle 1720 is inserted into the breast to extract a biopsy sample. The needle is visualized in the live 2D ultrasound image as shown in display window 1120 as ultrasound image 1820 as shown in FIG. 18B. Then in step 1922, the physician marks the biopsy needle path and the needle path is stored in a memory, such as the main memory 314, in the imaging system 100. As the physician performs multiple biopsies on the same patient P for the same area of interest, the physician marks each needle path and these needle paths are stored in a memory, such as the main memory 314, of the imaging system 100. From step 1922, the process proceeds to step 1932, such that as soon as the needle path is marked in a 2D ultrasound image, the imaging system 100 displays the needle path in the 3D display window 1110 as the needle image 1822 as shown in FIG. 18B. Then if the physician desires to review the biopsy needle paths, the process proceeds to step 1924 to review the needle paths by clicking on the Review Biopsy button 1878 in FIG. 18B, and the physician can then review and verify the biopsy needle paths for all the biopsies performed as shown in FIG. 18C. However, in the decision step 1906, if a seed placement/localization is to be performed, the process then proceeds to step 1940 to display a 2D live ultrasound image of the breast along with the image orientation 1872 and the image position 1874 of the ultrasound image 1822 as shown in FIG. 18B. Also, in step 1950, a 3D volume of the ultrasound images acquired in step 1904 is displayed in the display window 1110 as shown in FIG. 18B. Then in step 1942, the needle 1720 with seed marker 1760 is inserted into the breast and visualized in a 2D live ultrasound image similar to that visualized for biopsy in display window 1120 as needle image 1820 as in FIG. 18B. The physician marks the needle path as done in the step 1922. Then in step 1952, as soon as the physician marks the needle path in the 2D ultrasound image 1822, the needle path is then visualized as needle image 1822 in the 3D display window 1110 as, described in step 1932. Then in step 1946, once the seed marker 1760 is placed into the desired location in the tissue 1730 under ultrasound guidance provided by the imaging system 100, the physician marks the seed marker 1760 location in the 2D ultrasound image 1822 visualized in the display window 1120, as described in FIG. 18B. Then, in step 1956, the seed marker 1760 is visualized in 3D display window 1110.

As evident from the foregoing, the imaging system 100 can be used for a plurality of various treatments, procedures, or other therapeutic purposes, such as, for example, for prostate imaging and biopsy, as well as can be used for tissue extraction from a body. Also, the imaging system 100 can be used in addition to humans, can also be used for various research and medical application for animals, reptiles and other organisms, for example.

It is to be understood that the present invention is not limited to the embodiments described above, but encompasses any and all embodiments within the scope of the following claims.

I claim:

1. A tissue imaging system, comprising:
   an x-ray subsystem comprising an x-ray chamber, the x-ray chamber being a substantially rectangular chamber defined within a substantially rectangular housing, an x-ray beam generator and controller, an x-ray angle controller and an x-ray analysis processor and memory, the x-ray chamber having an x-ray tube disposed within the x-ray chamber, a digital flat panel detector spaced a predetermined distance and diametrically opposed in fixed and direct opposite-facing relation from the x-ray tube within the x-ray chamber, a specimen tray disposed between the x-ray tube and the digital flat panel detector, and a door on the x-ray chamber, the x-ray chamber enclosing the x-ray tube, the digital flat panel detector and the specimen tray within the x-ray chamber, wherein the x-ray analysis processor and memory includes a two dimensional (2D) and a three dimensional (3D) x-ray image generator for generating at least one 2D x-ray image and a 3D x-ray volume image from a plurality of 2D x-ray images of an extracted specimen, respectively, and a processor for at least one measurement and analysis of the x-ray images, the door of the x-ray chamber facilitating selective placement and removal of the extracted specimen respectively onto and from the specimen tray, the x-ray chamber being rotatable about an axis to facilitate angular positioning of the x-ray tube and the digital flat panel detector with respect to the specimen tray while maintaining the predetermined distance and fixed and direct opposite-facing relation between the x-ray tube and the digital flat panel detector throughout the angular positioning, rotation of the x-ray chamber being facilitated by rotation of the substantially rectangular housing;
   an ultrasound subsystem including an ultrasound probe with tracker system, an infrared 3D imaging camera, an ultrasound probe 3D position and orientation detector, an ultrasound beamformer, and an ultrasound analysis processor and memory, the ultrasound analysis processor and memory including an ultrasound 2D image generator for generating at least one 2D ultrasound image, an ultrasound position and angle calculator, and an ultrasound 3D volume generator for generating a 3D ultrasound volume image, and including a processor for at least one measurement and analysis of the ultrasound images, wherein the ultrasound subsystem creates a 3D ultrasound volume image from a plurality of 2D ultrasound images of an area of interest, the area of interest including the specimen to be extracted; and
   a processor controller system including an image fusion generator including a fusion processor and memory to fuse the 3D ultrasound volume image including the area of interest and the 3D x-ray volume image of the extracted specimen to form a fused image for at least one measurement and analysis of the fused image.

2. The tissue imaging system according to claim 1, wherein:
   the x-ray chamber rotates 360° around its axis to facilitate rotation of the x-ray tube and the digital flat panel detector 360° around the specimen tray inside the x-ray chamber, the specimen tray being stationary therein.

3. The tissue imaging system according to claim 1, wherein:
   the ultrasound subsystem creates the 3D ultrasound volume image from the plurality of 2D ultrasound images and one or more contoured structures in the area of interest based on the plurality of 2D ultrasound images, an ultrasound probe orientation and an ultrasound probe position.

4. The tissue imaging system according to claim 3, wherein:
the image fusion generator fuses the 3D ultrasound volume image including the one or more contoured structures in the area of interest and the 3D x-ray volume image of the extracted specimen.

5. The tissue imaging system according to claim 4, wherein:
the x-ray subsystem generates the 3D x-ray volume image of the extracted specimen placed in the specimen tray of the x-ray chamber.

6. The tissue imaging system according to claim 5, wherein:
the image fusion generator fuses the 3D ultrasound volume image including the one or more contoured structures in the area of interest and the 3D x-ray volume image of the extracted specimen and generates a 3D volume illustrating a combined 3D volume including the one or more contoured structures in the area of interest and the extracted specimen to provide at least a volume measurement, a height measurement, a length measurement and a width measurement for the one or more contoured structures and for the extracted specimen, respectively.

7. The tissue imaging system according to claim 6, wherein:
a difference in the measurements of the volume, the height, the length and the width between the extracted specimen and the one or more contoured structures are respectively determined from the generated combined 3D volume formed by the fused image of the 3D ultrasound volume image and the 3D x-ray volume image for quantitative analysis by the tissue imaging system.

8. A tissue imaging system, comprising:
an x-ray subsystem to generate at least one two dimensional (2D) x-ray image and a three dimensional (3D) x-ray volume image from a plurality of 2D x-ray images of an extracted specimen for at least one measurement and analysis of the x-ray images, the x-ray subsystem including an x-ray chamber having an x-ray tube disposed within the x-ray chamber, the x-ray chamber being a substantially rectangular chamber defined within a substantially rectangular housing, a digital flat panel detector spaced a predetermined distance and diametrically opposed in fixed and direct opposite-facing relation from the x-ray tube within the x-ray chamber, a specimen tray disposed between the x-ray tube and the digital flat panel detector, and a door on the x-ray chamber, the x-ray chamber enclosing the x-ray tube, the digital flat panel detector and the specimen tray within the x-ray chamber, the door of the x-ray chamber facilitating selective placement and removal of the extracted specimen respectively onto and from the specimen tray, the x-ray chamber being rotatable about an axis to facilitate angular positioning of the x-ray tube and the digital flat panel detector with respect to the specimen tray while maintaining the predetermined distance and fixed and direct opposite-facing relation between the x-ray tube and the digital flat panel detector throughout the angular positioning, rotation of the x-ray chamber being facilitated by rotation of the substantially rectangular housing;
an ultrasound subsystem including an ultrasound probe and an imaging camera to determine a position and orientation of a contoured structure in an area of interest that includes the specimen to be extracted and to generate at least one 2D ultrasound image including the contoured structure in the area of interest that includes the specimen to be extracted and to generate a 3D ultrasound volume image from a plurality of 2D ultrasound images including the contoured structure for at least one measurement and analysis of the ultrasound images; and
an image fusion generator including a fusion processor to fuse the 3D ultrasound volume image including the contoured structure and the 3D x-ray volume image of the extracted specimen to form a fused image for at least one measurement and analysis of the fused image.

9. The tissue imaging system according to claim 8, wherein:
the x-ray chamber rotates 360° around its axis to facilitate rotation of the x-ray tube and the digital flat panel detector 360° around the specimen tray inside the x-ray chamber, the specimen tray being stationary therein.

10. The tissue imaging system according to claim 9, wherein:
the x-ray subsystem generates the 3D x-ray volume image of the extracted specimen placed in the specimen tray of the x-ray chamber.

11. The tissue imaging system according to claim 8, wherein:
the ultrasound subsystem creates the 3D ultrasound volume image including the contoured structure based on a plurality of the generated at least one 2D ultrasound image.

12. The tissue imaging system according to claim 8, wherein:
the image fusion generator fuses the 3D ultrasound volume image including the contoured structure in the area of interest with the 3D x-ray volume image of the extracted specimen to create a combined 3D volume image forming the fused image.

13. The tissue imaging system according to claim 12, wherein:
the combined 3D volume image generated by the image fusion generator provides at least a volume measurement, a height measurement, a length measurement and a width measurement for the contoured structure and for the extracted specimen, respectively.

14. The tissue imaging system according to claim 13, wherein:
a difference in the measurements of the volume, the height, the length, and the width between the contoured structure and the extracted specimen are respectively determined from the fused image generated by the image fusion generator for quantitative analysis of the fused image by the tissue imaging system.

* * * * *